(12) United States Patent
Kakinuma

(10) Patent No.: US 12,275,814 B2
(45) Date of Patent: Apr. 15, 2025

(54) (METH)ACRYLATE, MONOMER COMPOSITION, MOLDED BODY, COMPOSITION FOR DENTAL MATERIAL, AND DENTAL MATERIAL

(71) Applicant: MITSUI CHEMICALS, INC., Tokyo (JP)

(72) Inventor: Naoyuki Kakinuma, Ichihara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 987 days.

(21) Appl. No.: 17/292,866

(22) PCT Filed: Dec. 11, 2019

(86) PCT No.: PCT/JP2019/048500
§ 371 (c)(1),
(2) Date: May 11, 2021

(87) PCT Pub. No.: WO2020/122124
PCT Pub. Date: Jun. 18, 2020

(65) Prior Publication Data
US 2021/0403632 A1 Dec. 30, 2021

(30) Foreign Application Priority Data
Dec. 11, 2018 (JP) .................. 2018-231945

(51) Int. Cl.
| | |
|---|---|
| *A61K 6/887* | (2020.01) |
| *C07C 69/54* | (2006.01) |
| *C08F 290/06* | (2006.01) |
| *C08G 18/24* | (2006.01) |
| *C08G 18/67* | (2006.01) |

(Continued)

(52) U.S. Cl.
CPC ............ *C08G 18/672* (2013.01); *A61K 6/887* (2020.01); *C07C 69/54* (2013.01); *C08F 290/067* (2013.01); *C08G 18/246* (2013.01); *C08G 18/73* (2013.01); *C08G 18/755* (2013.01); *C08G 18/757* (2013.01); *C08G 18/758* (2013.01);
(Continued)

(58) Field of Classification Search
CPC ................................ A61K 6/887; C08L 33/10
See application file for complete search history.

(56) References Cited

U.S. PATENT DOCUMENTS

| | | | |
|---|---|---|---|
| 5,470,689 A | 11/1995 | Wolf et al. | |
| 10,975,260 B2 * | 4/2021 | Liu | ............... C08K 5/3415 |

(Continued)

FOREIGN PATENT DOCUMENTS

| | | |
|---|---|---|
| CN | 106543093 A | 3/2017 |
| EP | 2 711 381 A1 | 3/2014 |

(Continued)

OTHER PUBLICATIONS

Epoxy Ester Oligomer (Year: 2024).*

*Primary Examiner* — Peter A Salamon
(74) *Attorney, Agent, or Firm* — BUCHANAN INGERSOLL & ROONEY PC

(57) ABSTRACT

A (meth)acrylate includes a compound (X) having a structure formed by a reaction of an epoxy compound (A) containing an epoxy group and a tertiary carbon atom or a quaternary carbon atom, a (meth)acrylic acid (B), and an iso(thio)cyanate compound (C) having two or more iso(thio)cyanate groups.

12 Claims, 14 Drawing Sheets

(51) Int. Cl.
*C08G 18/73* (2006.01)
*C08G 18/75* (2006.01)
*C08G 18/76* (2006.01)

(52) U.S. Cl.
CPC ....... *C08G 18/7642* (2013.01); *C08G 18/765* (2013.01)

(56) References Cited

U.S. PATENT DOCUMENTS

| | | |
|---|---|---|
| 2007/0142495 A1 | 6/2007 | Neffgen et al. |
| 2010/0307378 A1* | 12/2010 | Trujillo-Lemon .... C07C 271/24 106/35 |
| 2014/0091250 A1* | 4/2014 | Omura ................. C08G 18/835 525/450 |
| 2018/0180995 A1 | 6/2018 | Choi et al. |
| 2018/0327627 A1* | 11/2018 | Liu ...................... C09D 133/24 |

FOREIGN PATENT DOCUMENTS

| | | |
|---|---|---|
| JP | H072940 A | 1/1995 |
| JP | 2005089312 A | 4/2005 |
| JP | 2005187385 A | 7/2005 |
| JP | 2006328237 A | 12/2006 |
| JP | 2007015946 A | 1/2007 |
| JP | 2007526270 A | 9/2007 |
| JP | 2018528447 A | 9/2018 |
| WO | WO-2018043127 A1 * | 3/2018 ............... B32B 9/00 |

* cited by examiner

(METH)ACRYLATE, MONOMER COMPOSITION, MOLDED BODY, COMPOSITION FOR DENTAL MATERIAL, AND DENTAL MATERIAL

TECHNICAL FIELD

The present invention relates to a (meth)acrylate, a monomer composition, a molded body, a composition for a dental material, and a dental material.

Conventionally, polymerizable monomers represented by (meth)acrylates are widely used in various fields such as paints, printing plates, optical materials, and dental materials by utilizing their properties such as good curability and transparency.

In the field of dental materials, polymerizable monomers are widely used in dental restorative materials such as dental composite resins used for repairing dental caries and fractures of natural teeth, various dental adhesives used to bond dental composite resins to teeth, as well as artificial teeth, denture base materials, and the like.

Dental composite resins are generally composed of a polymerizable monomer, a polymerization initiator and a filler, and from the viewpoint of in-vivo safety, mechanical strength of a cured product, abrasion resistance, aesthetics, and the like, radical-polymerizable polyfunctional (meth)acrylates are used. As radical-polymerizable polyfunctional (meth)acrylates, 2,2-bis[4-(3-methacryloyloxy-2-hydroxypropoxy)phenyl]propane (commonly known as Bis-GMA), and 2,2,4-trimethylhexamethylenebis(2-carbamoyloxyethyl)dimethacrylate (commonly known as UDMA) are used.

However, regarding dental composite resins, it has been pointed out that there is much room for improvement in reducing polymerization shrinkage during curing. It is desired to reduce polymerization shrinkage since it causes a contraction gap caused by the dental composite resin peeling off from the adhesive surface and causes secondary caries, tooth pulp stimulation, coloring, and restoration material falling.

In order to reduce polymerization shrinkage, it is generally proposed to use a ring-opening polymerizable epoxy compound or an oxetane compound with less polymerization shrinkage than an acrylic compound (for example, see Patent Literature 1 and Patent Literature 2).

Further, it is also proposed to increase the filling amount of filler and to reduce polymerization shrinkage (for example, see Patent Literature 3 and Patent Literature 4).

[Patent Literature 1] Japanese National-Phase Publication (JP-A) No. 2007-15946
[Patent Literature 2] JP-A No. 2005-187385
[Patent Literature 3] JP-A No. 2007-526270
[Patent Literature 4] JP-A No. 2005-89312

SUMMARY OF INVENTION

Technical Problem

In Patent Literature 1 and Patent Literature 2, polymerization shrinkage tends to be reduced by using these compounds, but there are many problems such as the need for a dedicated primer since the curing system is different.

Further, in Patent Literature 3 and Patent Literature 4, since the shrinkage rate of the monomer used is high, the effect is limited.

Further, as the (meth) acrylate used for a dental composite resin or the like, it is desirable that mechanical strength such as breaking strength can be increased when it is made into a cured product.

One aspect of the present invention is made in view of the above problem, and an object thereof is to provide a (meth)acrylate capable of manufacturing a cured product with excellent breaking strength, and less polymerization shrinkage during curing, a monomer composition containing thereof, a molded body including a cured product of this monomer composition, a composition for a dental material containing this monomer composition, and a dental material including a cured product of this composition for a dental material.

Solution to Problem

Examples of the means for solving the above problem are shown below.

<1> A (meth)acrylate comprising a compound (X) having a structure formed by a reaction of an epoxy compound (A) containing an epoxy group and a tertiary carbon atom or a quaternary carbon atom, a (meth)acrylic acid (B), and an iso(thio)cyanate compound (C) having two or more iso(thio)cyanate groups.

<2> The (meth)acrylate according to <1>, wherein the compound (X) is a reaction product of a reactant of the epoxy compound (A) and the (meth)acrylic acid (B), and the iso(thio)cyanate compound (C).

<3> The (meth)acrylate according to <1> or <2>, wherein the epoxy compound (A) comprises a tert-butyl group, a tert-pentyl group, a tert-hexyl group, a tert-heptyl group, a tert-octyl group, a tert-nonyl group, a tert-decyl group or a cumyl group.

<4> The (meth)acrylate according to any one of <1> to <3>, wherein the epoxy compound (A) comprises a glycidyl ether group that is a functional group containing the epoxy group.

<5> The (meth)acrylate according to <4>, represented by the following general formula (1).

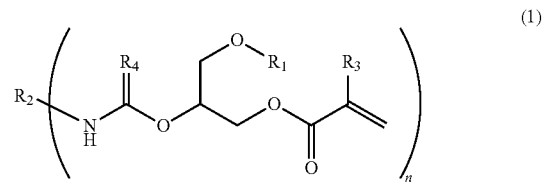

Wherein, in general formula (1), $R_1$ represents a residue of the epoxy compound (A) from which the glycidyl ether group has been removed; $R_2$ represents a residue of the iso(thio)cyanate compound (C) from which all iso(thio)cyanate groups have been removed; $R_3$ represents a hydrogen atom or a methyl group; $R_4$ represents an oxygen atom or a sulfur atom; n is an integer of 2 or more; and plural instances of $R_1$, $R_3$ and $R_4$ may be the same or different, respectively.

<6> The (meth)acrylate according to <5>, wherein a molecular weight of the $R_1$ is from 50 to 300 in general formula (1).

<7> The (meth)acrylate according to <5>, wherein $R_1$ is a group represented by the following formula (2), (3), (4), (5), (6), (7), (8), (9) or (10) in general formula (1).

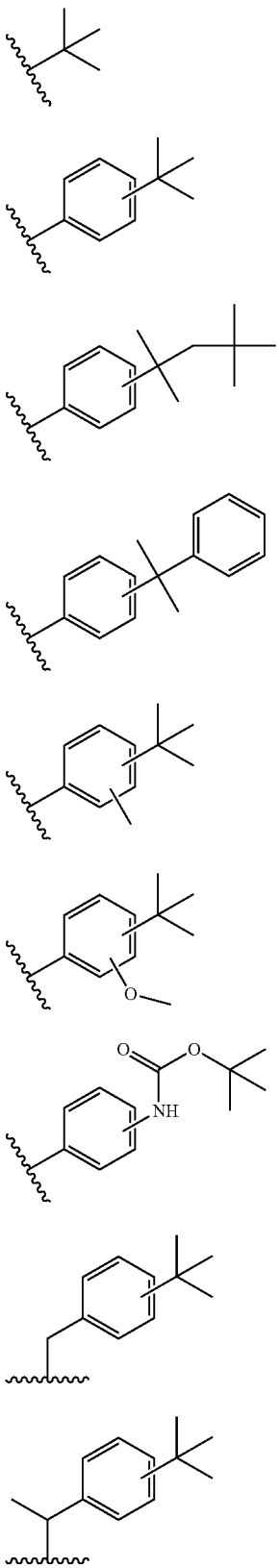

Wherein, in formulae (2)-(10), each wavy line represents a binding site.

<8> The (meth)acrylate according to any one of <1> to <7>, wherein the iso(thio)cyanate compound (C) is at least one kind of iso(thio)cyanate compound selected by the group consisting of hexamethylene diisocyanate, 2,2,4-trimethylhexamethylene diisocyanate, 2,4,4-trimethylhexamethylene diisocyanate, pentamethylene diisocyanate, m-xylylene diisocyanate, 1,3-tetramethylxylylene diisocyanate, isophorone diisocyanate, bis(isocyanatemethyl)cyclohexane, bis(isocyanatecyclohexyl)methane, 2,5-bis(isocyanatemethyl)bicyclo-[2.2.1]-heptane, 2,6-bis(isocyanatemethyl)bicyclo-[2.2.1]-heptane, tolylene diisocyanate, phenylene diisocyanate, and 4,4'-diphenylmethane diisocyanate.

<9> A (meth)acrylate comprising a (meth)acryloyloxy group, an urethane bond, and a structure represented by the following general formula (1-1).

(1-1)

In general formula (1-1), $R^1$ represents a tertiary carbon atom or a quaternary carbon atom; and *1 and *2 represent a binding site.

<10> A monomer composition comprising a (meth)acrylate (D) that is the (meth)acrylate according to any one of <1> to <9>.

<11> A molded body comprising a cured product of the (meth)acrylate according to any one of <1> to <9> or a cured product of the monomer composition according to <10>.

<12> A composition for a dental material comprising the (meth)acrylate according to any one of <1> to <9> or the monomer composition according to <10>, a polymerization initiator, and a filler.

<13> A dental material comprising a cured product of the composition for a dental material according to <12>.

Advantageous Effects of Invention

One aspect of the present invention enables to provide a (meth)acrylate capable of manufacturing a cured product with excellent breaking strength, and less polymerization shrinkage during curing, a monomer composition containing thereof, a molded body including a cured product of this monomer composition, a composition for a dental material containing this monomer composition, and a dental material including a cured product of this composition for a dental material.

DESCRIPTION OF EMBODIMENTS

Mode for Carrying Out the Invention

Figure 1:
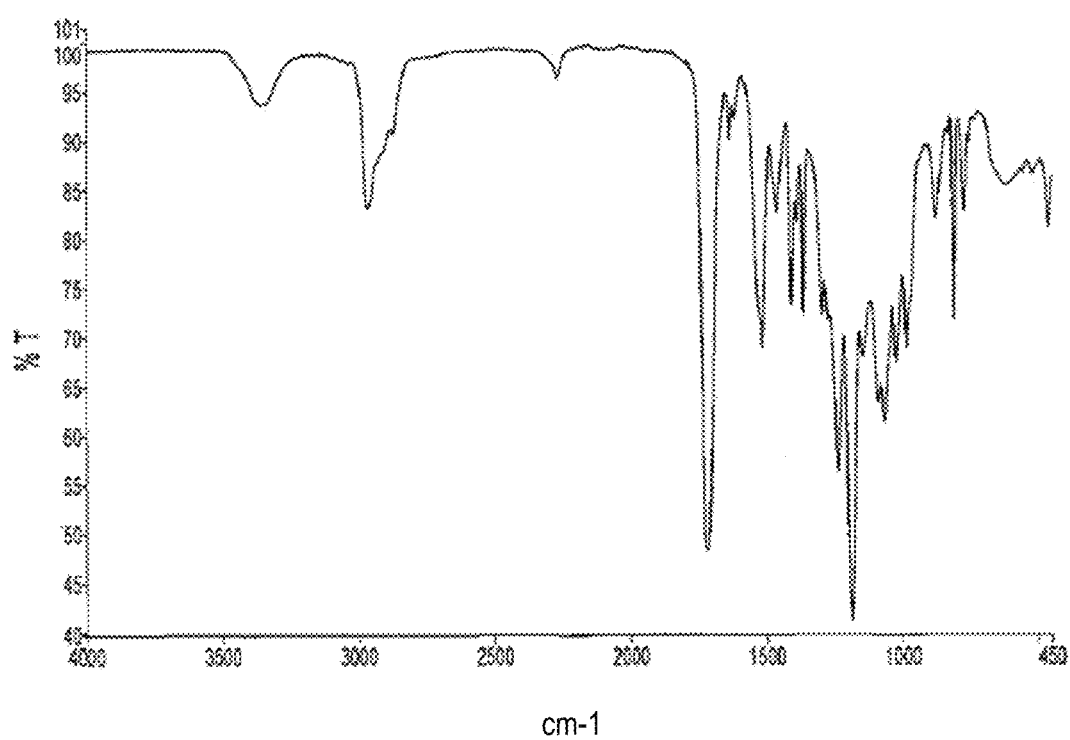
FIG. 1 shows IR spectrum of urethane diacrylate (A-1) obtained in Example 1.
Figure 2:
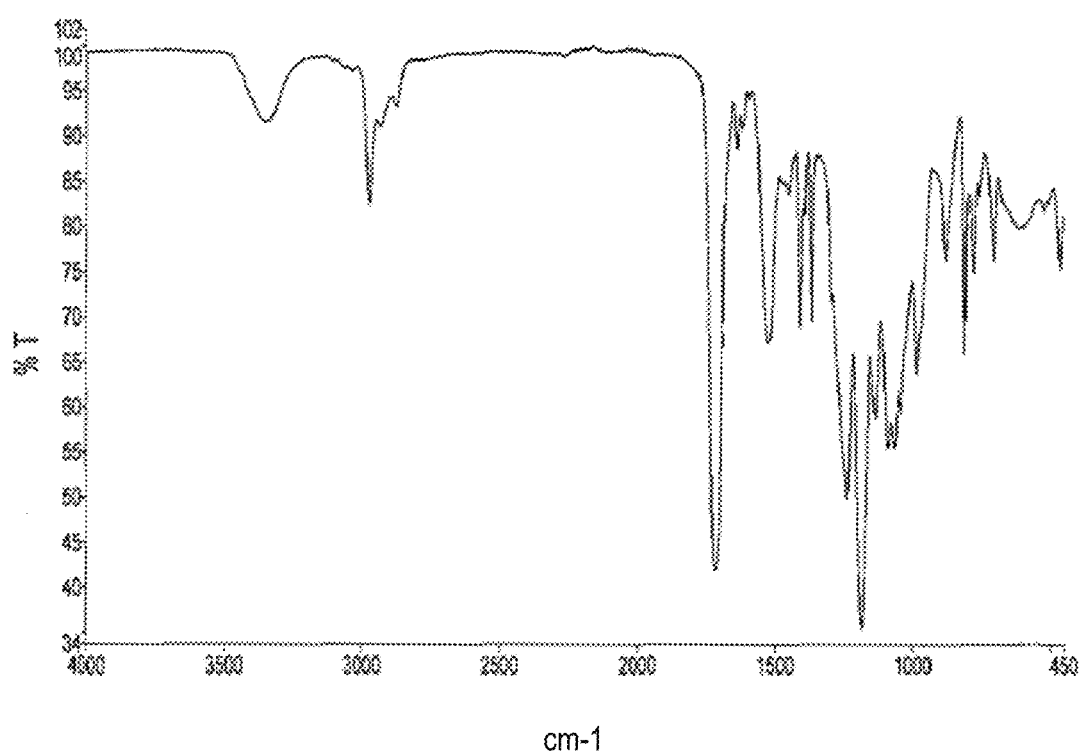
FIG. 2 shows IR spectrum of urethane diacrylate (A-2) obtained in Example 2.
Figure 3:
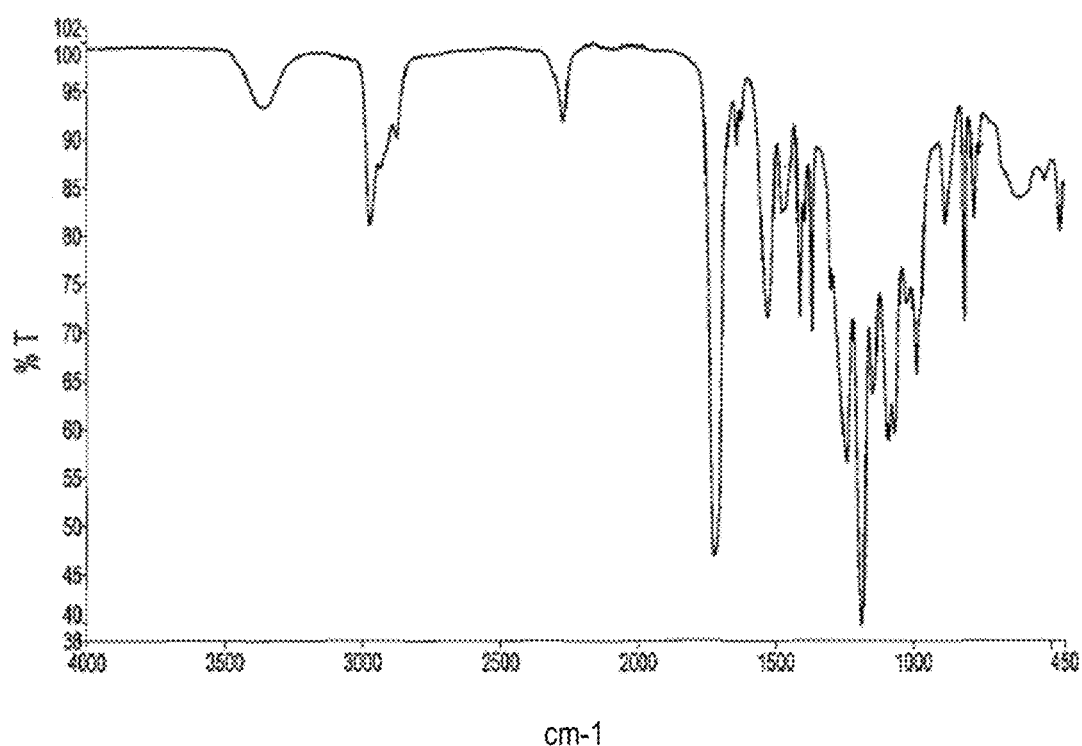
FIG. 3 shows IR spectrum of urethane diacrylate (A-3) obtained in Example 3.
Figure 4:
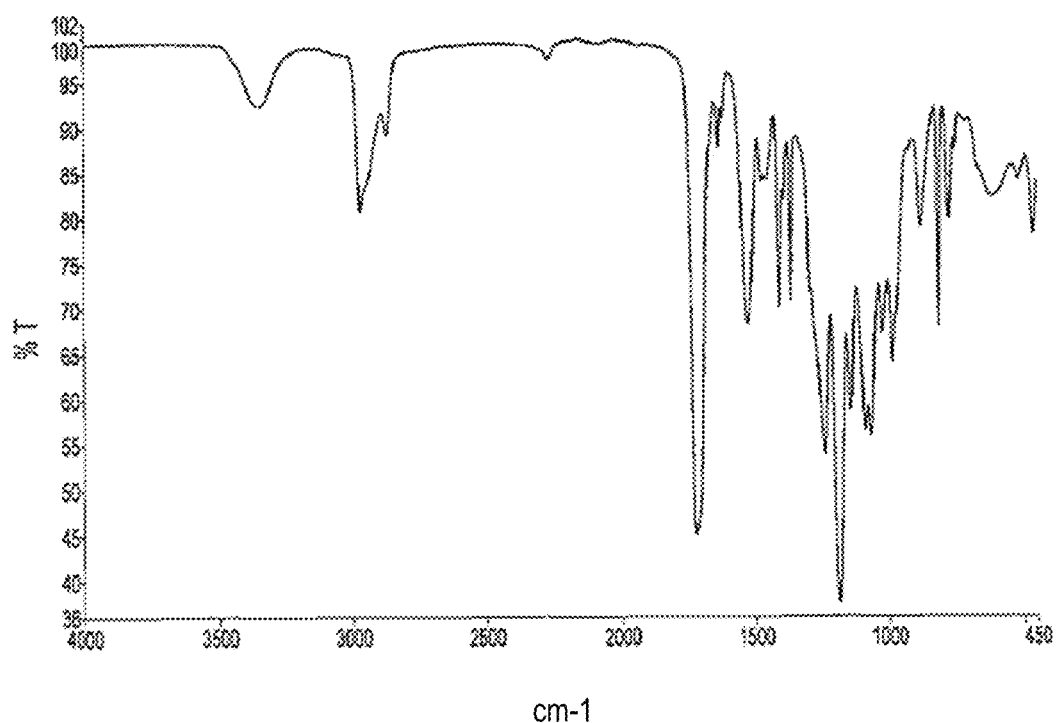
FIG. 4 shows IR spectrum of urethane diacrylate (A-4) obtained in Example 4.
Figure 5:
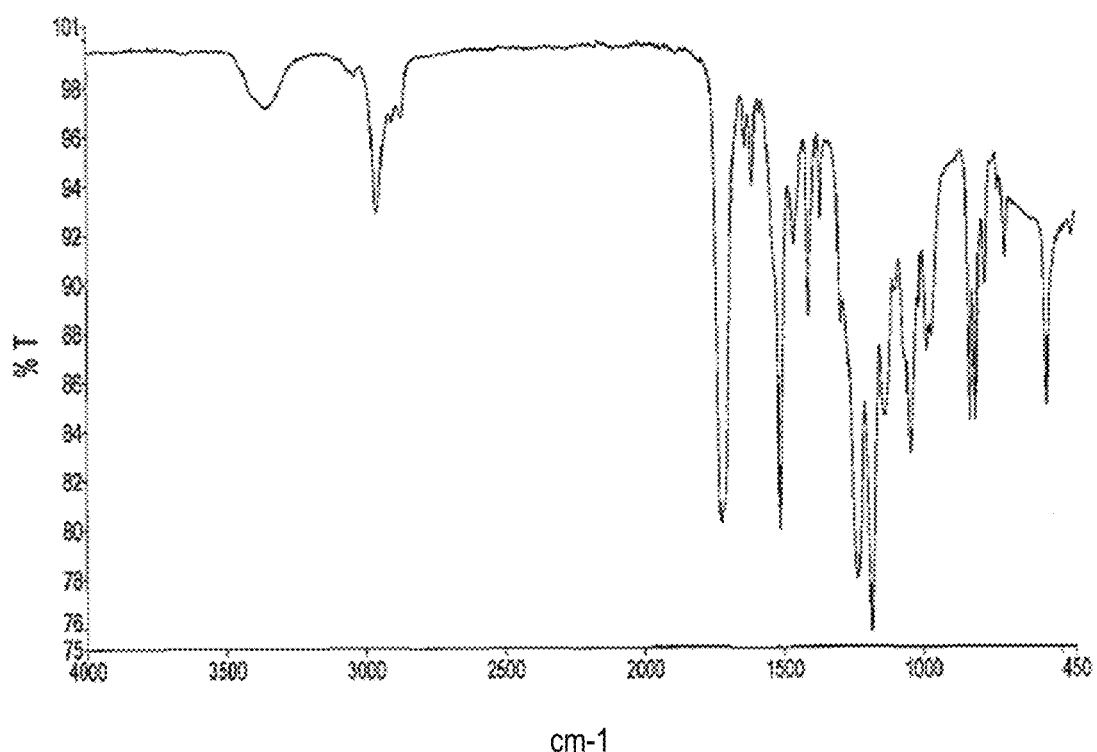
FIG. 5 shows IR spectrum of urethane diacrylate (A-5) obtained in Example 5.
Figure 6:
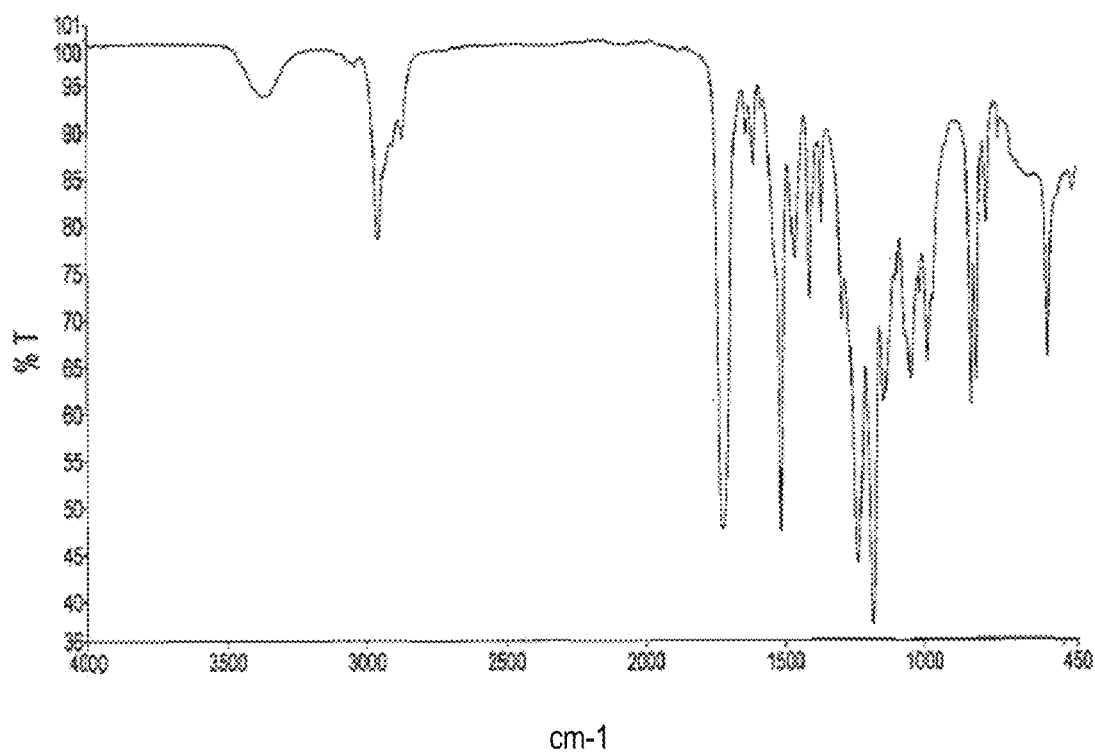
FIG. 6 shows IR spectrum of urethane diacrylate (A-6) obtained in Example 6.
Figure 7:
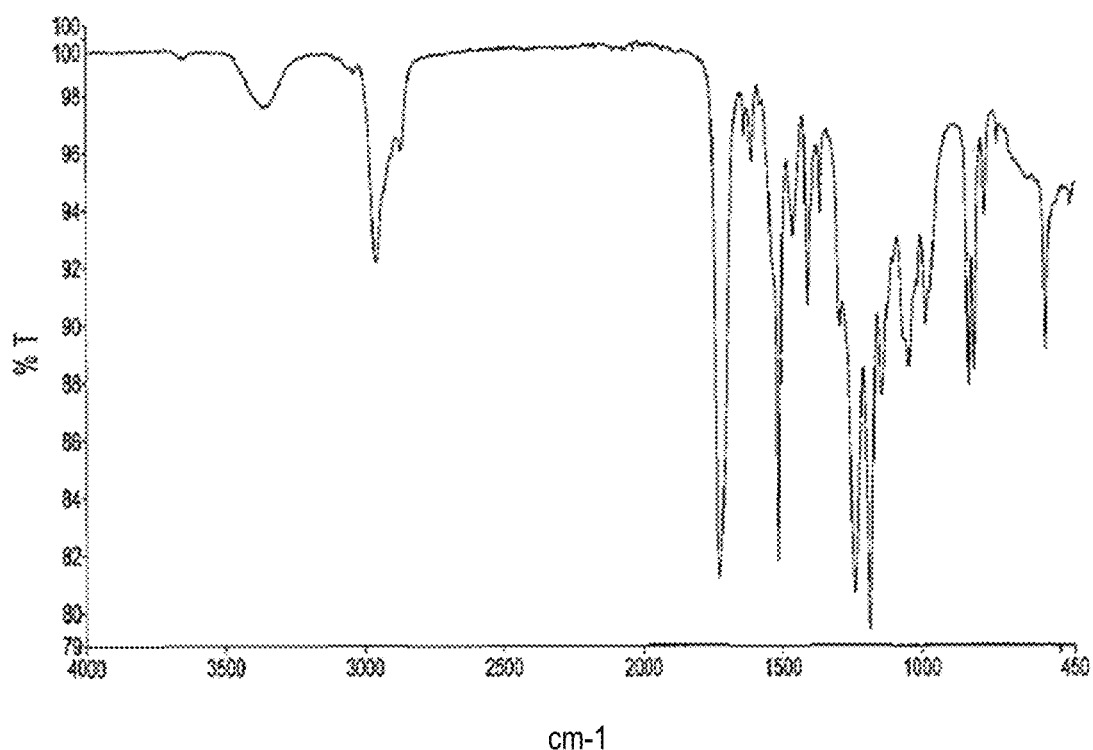
FIG. 7 shows IR spectrum of urethane diacrylate (A-7) obtained in Example 7.
Figure 8:
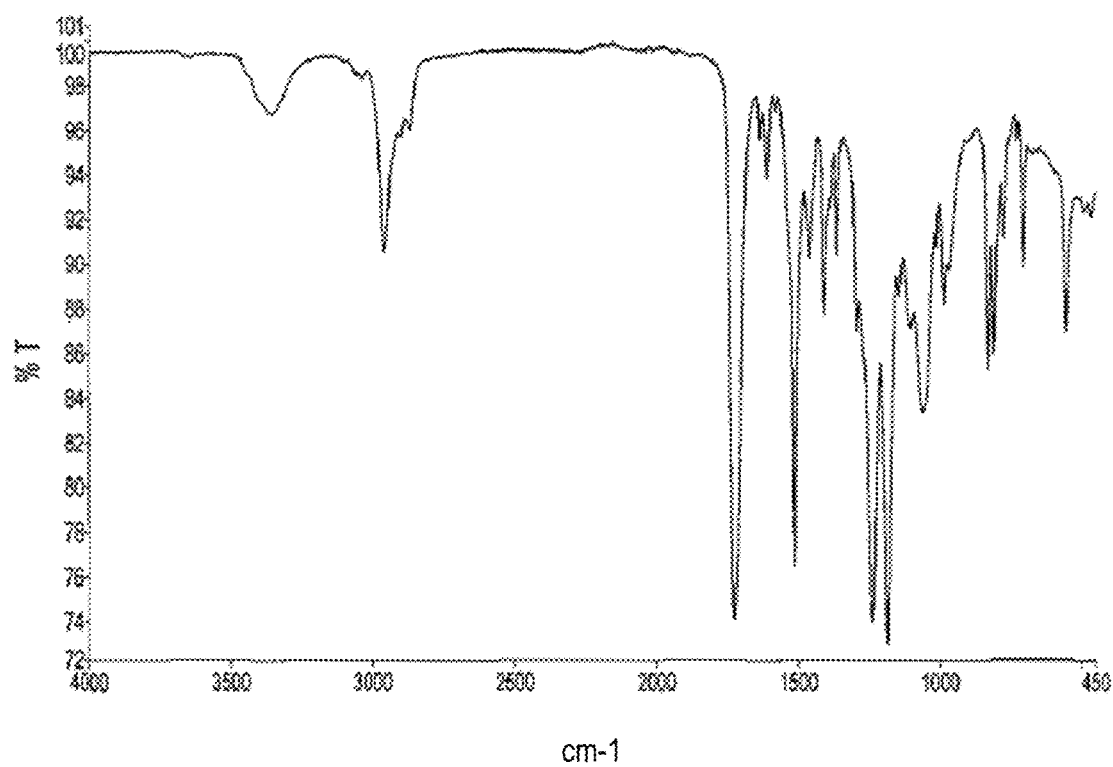
FIG. 8 shows IR spectrum of urethane diacrylate (A-8) obtained in Example 8.
Figure 9:
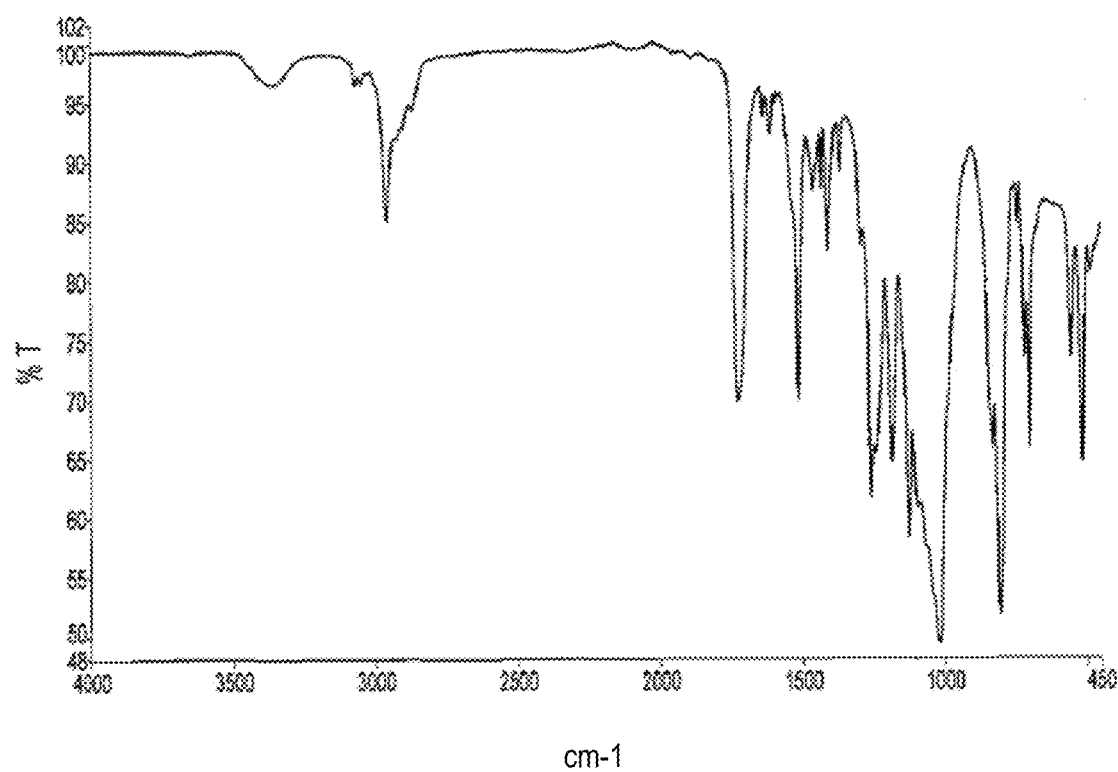
FIG. 9 shows IR spectrum of urethane diacrylate (A-9) obtained in Example 9.
Figure 10:
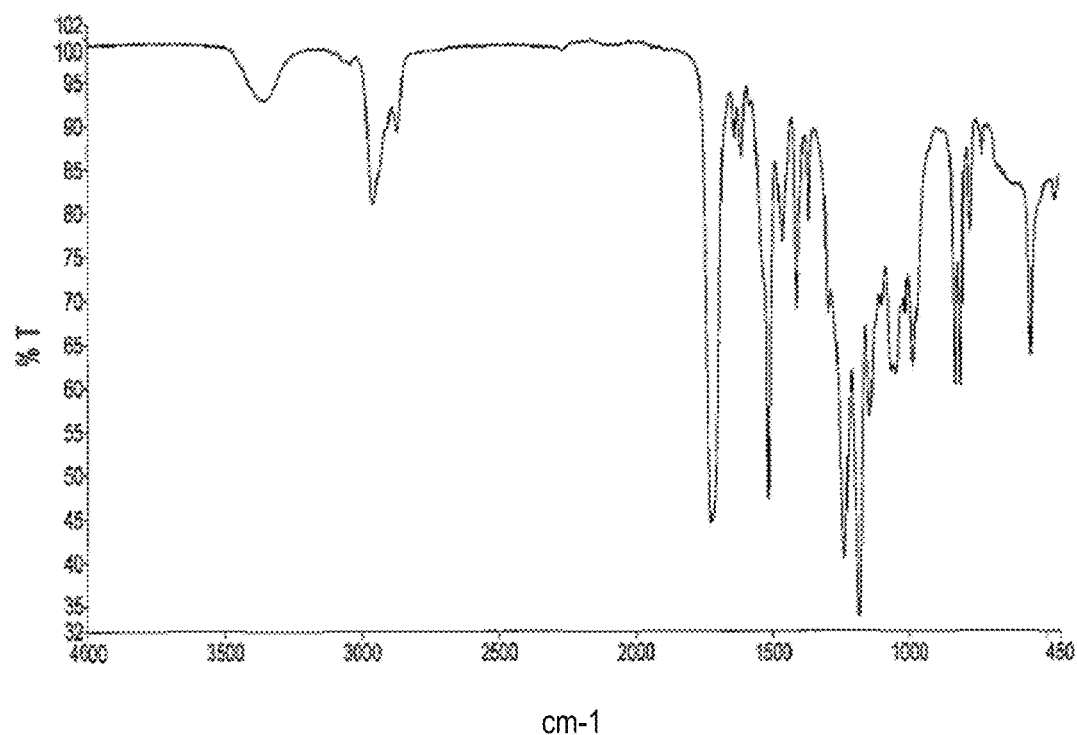
FIG. 10 shows IR spectrum of urethane diacrylate (A-10) obtained in Example 10.
Figure 11:
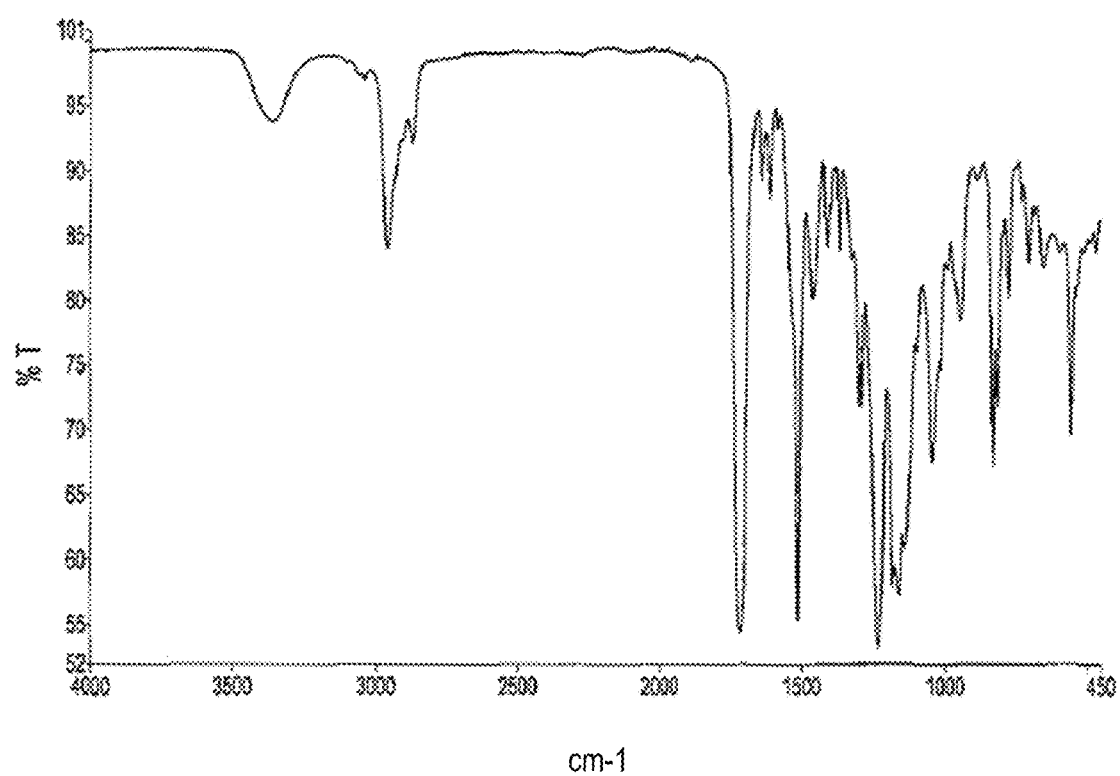
FIG. 11 shows IR spectrum of urethane diacrylate (A-11) obtained in Example 11.
Figure 12:
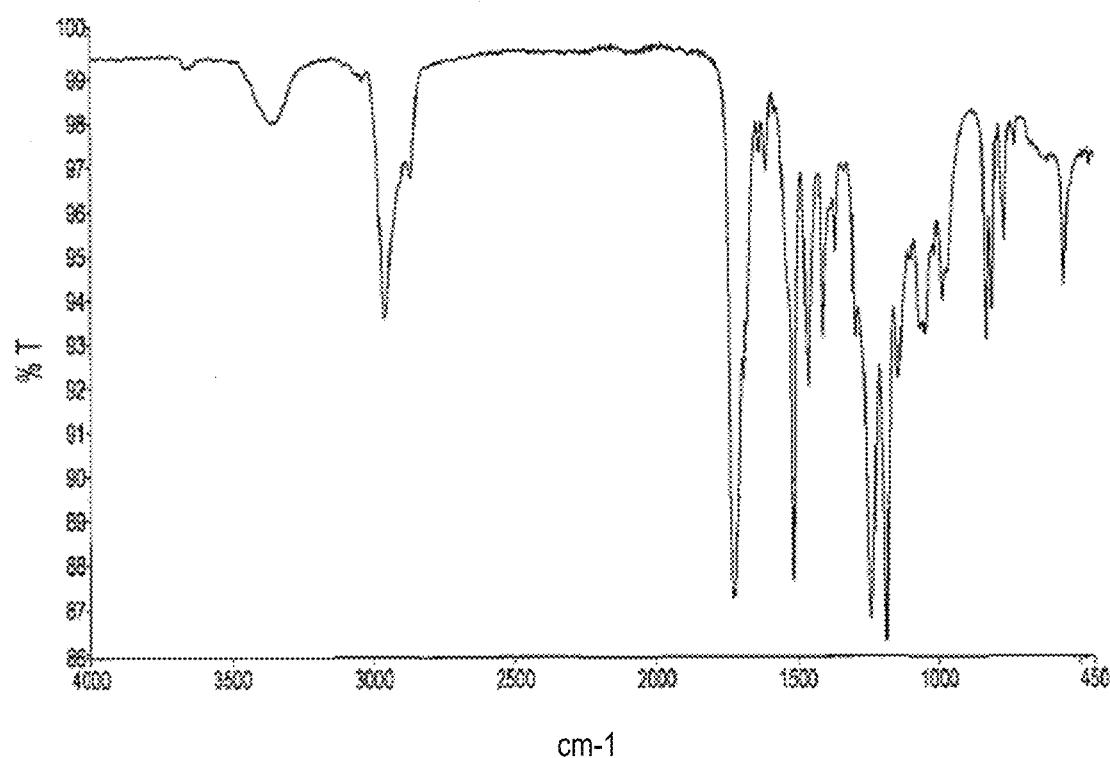
FIG. 12 shows IR spectrum of urethane diacrylate (A-12) obtained in Example 12.
Figure 13:
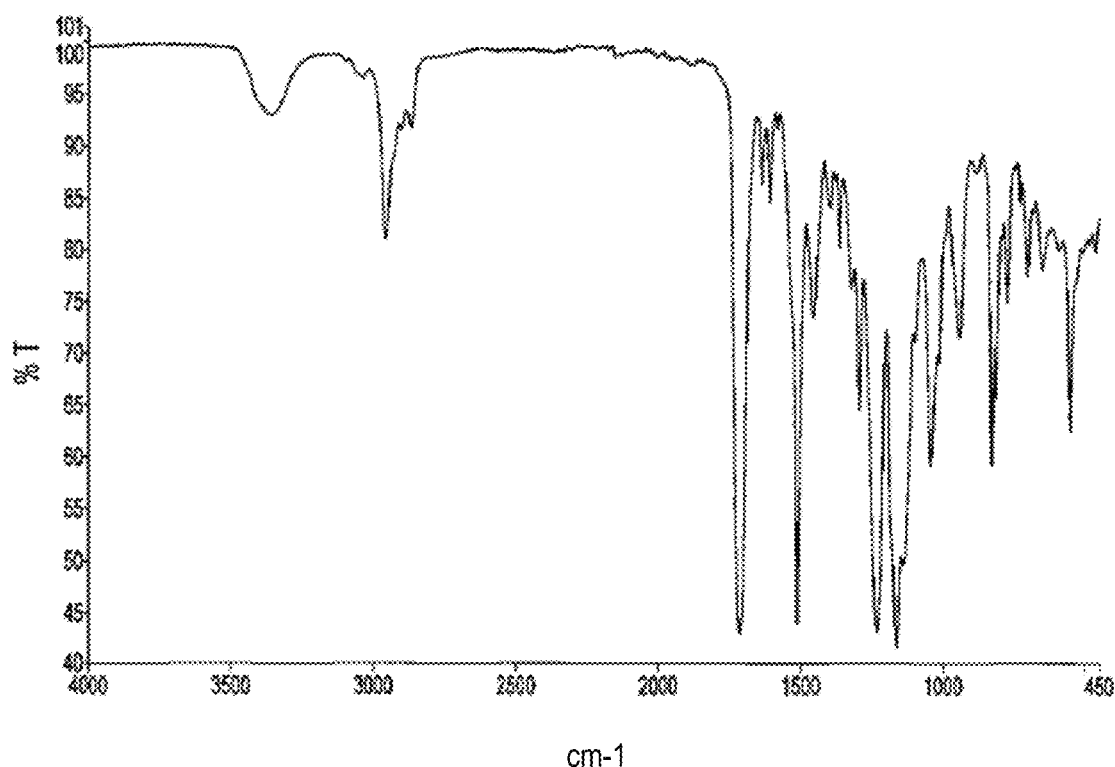
FIG. 13 shows IR spectrum of urethane dimethacrylate (M-1) obtained in Example 13.
Figure 14:
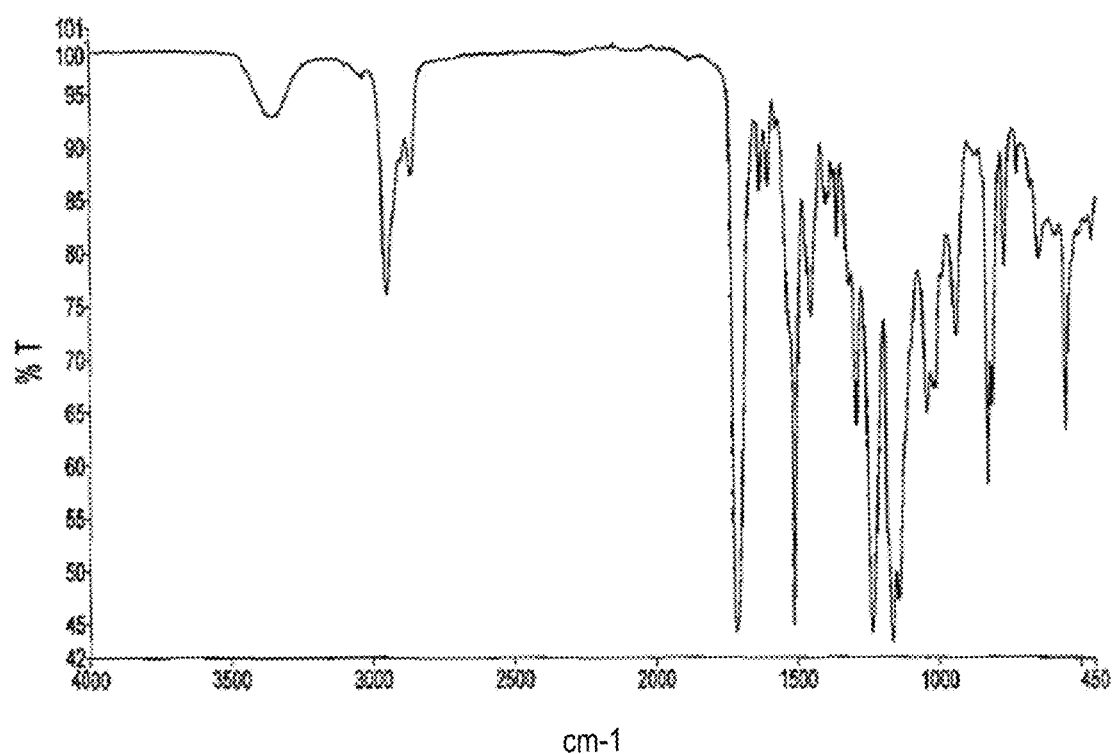
FIG. 14 shows IR spectrum of urethane dimethacrylate (M-2) obtained in Example 14.

Embodiments of the invention are described below in detail. It is noted here, however, that the invention is not limited to the below-described embodiments. In the below-described embodiments, the constituents thereof (including element steps and the like) are not indispensable unless otherwise specified. The same applies to the numerical values and ranges thereof, without restricting the invention.

In the present disclosure, those numerical ranges that are stated with "to" each denote a range that includes the numerical values stated before and after "to" as the lower and upper limit values, respectively.

In a set of numerical ranges that are stated stepwise in the disclosure, the upper limit value or the lower limit value of a numerical range may be replaced with an upper limit value or a lower limit value of other numerical range. Further, in a numerical range stated in the disclosure, the upper limit or the lower limit of the numerical range may be replaced with a relevant value indicated in any of Examples.

In the present disclosure, "(meth)acryloyl" means acryloyl or methacryloyl, and "(meth)acrylate" means acrylate or methacrylate.

In the present disclosure, "iso(thio)cyanate" means isocyanate or isothiocyanate.

In the present disclosure, "urethane" includes product formed by the reaction of a hydroxy group of a hydroxy (meth)acrylate and an isocyanate group of an isocyanate compound and product formed by the reaction of a hydroxy group of a hydroxy(meth)acrylate and an isothiocyanate group of an isothiocyanate compound.

[(Meth)Acrylate]

A (meth)acrylate (hereinafter, it is also referred to as "(meth)acrylate (D)") in the present disclosure is a compound (X) having a structure formed by a reaction of an epoxy compound (A) containing an epoxy group and a tertiary carbon atom or a quaternary carbon atom, a (meth) acrylic acid (B), and an iso(thio)cyanate compound (C) having two or more iso(thio)cyanate groups. Since the (meth)acrylate (D) is a compound having the above-described structure, it is possible to form the cured product with excellent breaking strength and make polymerization shrinkage less during curing.

The compound (X) is not limited to the reaction product obtained by reacting the epoxy compound (A), the (meth) acrylic acid (B), and the iso(thio)cyanate compound (C) as raw materials, and includes all compounds having the same structure as this reaction product.

The above-described compound (X) is preferably the reaction product of the epoxy compound (A), the (meth) acrylic acid (B), and the iso(thio)cyanate compound (C), and is preferably the reaction product of the reactant of the epoxy compound (A) and the (meth)acrylic acid (B), and the iso(thio)cyanate compound (C). The above-described reactant is preferably a hydroxy(meth)acrylate formed by a reaction of an epoxy group of the epoxy compound (A) and a carboxy group of the (meth)acrylic acid (B). The above-described reaction product is preferably the reaction product having a urethane bond formed by a reaction of a hydroxy group of the hydroxy(meth)acrylate which is the above-described reactant and an iso(thio)cyanate group of the iso(thio)cyanate compound (C).

(Epoxy Compound (A))

The epoxy compound (A) is a compound containing an epoxy group and a tertiary carbon atom or a quaternary carbon atom, and is preferably a compound containing an epoxy group and a tertiary carbon atom or a quaternary carbon atom bonding the epoxy group directly or via a divalent linking group. By using the epoxy compound (A) containing a tertiary carbon atom or a quaternary carbon atom for production of the reaction product, it is possible to form the cured product with excellent breaking strength and make polymerization shrinkage less during curing. When the epoxy compound (A) contains a tertiary carbon, it is preferable that the epoxy group and the tertiary carbon atom are directly bonded. When the epoxy compound (A) contains a quaternary carbon atom, it is preferable that the epoxy group and the quaternary carbon atom are bonded via a divalent linking group. Particularly, from the point of capable of forming the cured product with excellent breaking strength, the epoxy compound (A) preferably contains a tertiary carbon atom directly bonded to the epoxy group.

Examples of divalent linking group which may be contained in the epoxy compound (A) are not particularly limited and include an alkylene group, an arylene group, —C(=O)—, —SO$_2$—, —NR— (R represents a hydrogen atom or an alkyl group having 1 to 10 carbon atoms, and preferably a hydrogen atom), a group consisting of a combination thereof and the like. As the divalent linking group, an alkylene group and an arylene group are preferable.

The carbon number of the alkylene group is preferably from 1 to 20, more preferably from 1 to 10 and still more preferably from 1 to 5. The alkylene group may have a substituent or may be unsubstituted. The alkylene group may be linear, branched or cyclic. The cyclic alkylene group may be monocyclic or polycyclic. Specific examples of the alkylene group include an ethylene group, an n-propylene group, an isopropylene group, an n-butylene group, an isobutylene group, a sec-butylene group, a tert-butylene group, an n-pentylene group, an isopentylene group and a neopentylene group and a tert-pentylene group.

The carbon number of the arylene group is preferably from 6 to 18, more preferably from 6 to 14, and still more preferably from 6 to 10. Specific examples of the arylene group include an o-phenylene group, an m-phenylene group, a p-phenylene group, and a divalent condensed polycyclic aromatic ring group in which two or more aromatic rings are condensed.

The tertiary carbon atom or the quaternary carbon atom may be any carbon atom having three or four adjacent carbon atoms, and may be preferably any carbon atom bonding an epoxy group directly or via a divalent linking group and having three or four adjacent carbon atoms. In other words, the epoxy compound (A) just has a structure (structure containing a tertiary carbon atom or a quaternary carbon atom) containing a carbon atom having three or four adjacent carbon atoms, and preferably just has a structure a carbon atom bonding an epoxy group directly or via a divalent linking group and having three or four adjacent carbon atoms.

Examples of a structure containing the tertiary carbon atom or the quaternary carbon atom include an isopropyl group, an isobutyl group, a sec-butyl group, a tert-butyl group, an isopentyl group, a neopentyl group, a tert-pentyl group, an isohexyl group, a sec-hexyl group, a tert-hexyl group, an isoheptyl group, a sec-heptyl group, a tert-heptyl group, an isooctyl group, a sec-octyl group, a tert-octyl group, an isononyl group, a sec-nonyl group, a tert-nonyl group, an isodecyl group, a sec-decyl group, a tert-decyl group and a cumyl group.

When a carbon atom which can be the tertiary carbon atom or the quaternary carbon atom is bonded to a carbon atom of a divalent linking group, the number of the adjacent carbon atom includes a carbon atom of the divalent linking group. For example, when the divalent linking group is a p-phenylene group, and the p-phenylene group is bonded to a tert-butyl group, the epoxy compound (A) is interpreted to contain the quaternary carbon atom.

The structure containing the tertiary carbon atom or the quaternary carbon atom is preferably a structure in which a hydrogen atom is not bonded to the carbon atom, and more specifically, the structure is preferably a tert-butyl group, a tert-pentyl group, a tert-hexyl group, a tert-heptyl group, a tert-octyl group, a tert-nonyl group, a tert-decyl group, a cumyl group or the like.

The epoxy compound (A) may contain a glycidyl ether group, a glycidyl amine group, a glycidyl ester group and the like as a functional group containing an epoxy group. Among them, the epoxy compound (A) preferably contain a glycidyl ether group as the functional group containing an epoxy group.

The specific example of the epoxy compound (A) include tert-butyl glycidyl ether, 4-tert-butyl phenyl glycidyl ether, 4-tert-octyl phenyl glycidyl ether, and 4-cumyl phenyl glycidyl ether. Of these, from the point of capable of forming the cured product with excellent breaking strength, tert-butylglycidyl ether is preferable.

The epoxy compound (A) may be used singly or in combination of two or more.

((Meth)Acrylic Acid (B))

The (meth)acrylic acid (B) is acrylic acid or methacrylic acid. A carboxy group of the (meth)acrylic acid (B) will react with an epoxy group of the epoxy compound (A), and for example the above-described reactant will be obtained by a reaction of an epoxy group of the epoxy compound (A) and a carboxy group of the (meth)acrylic acid (B).

When the epoxy compound (A), the (meth)acrylic acid (B), and the iso(thio)cyanate compound (C) are reacted and when the epoxy compound (A) and the (meth)acrylic acid (B) are reacted, a ratio ($\beta/\alpha$) of number ($\beta$) of moles of an epoxy group in the epoxy compound (A) with respect to number ($\alpha$) of moles of the (meth)acrylic acid (B) is preferably from 0.5 to 1.2, is more preferably from 0.8 to 1.1, and is still more preferably from 0.9 to 1.0.

As the (meth)acrylic acid (B), acrylic acid or methacrylic acid may be used singly or acrylic acid and methacrylic acid may be used in combination.

(Iso(Thio)Cyanate Compound (C))

The iso(thio)cyanate compound (C) is a compound having two or more iso(thio)cyanate groups, and is preferably a compound having two or three iso(thio)cyanate groups. An iso(thio)cyanate group of the iso(thio)cyanate compound (C) will be reacted with a hydroxy group of the above-described reactant, and for example the above-described reaction product will be obtained by a reaction of a hydroxy group of the above-described reactant and an iso(thio)cyanate group of the iso(thio)cyanate compound (C).

Examples of the isocyanate compound (C) include hexamethylene diisocyanate, 2,2,4-trimethylhexamethylene diisocyanate, 2,4,4-trimethylhexamethylene diisocyanate, pentamethylene diisocyanate, m-xylylene diisocyanate, 1,3-tetramethylxylylene diisocyanate, isophorone diisocyanate, bis(isocyanatemethyl)cyclohexane, bis(isocyanatecyclohexyl)methane, 2,5-bis(isocyanatemethyl)bicyclo-[2.2.1]-heptane, 2,6-bis(isocyanatemethyl)bicyclo-[2.2.1]-heptane, tolylene diisocyanate, phenylene diisocyanate, and 4,4'-diphenylmethane diisocyanate. The isocyanate compound (C) may be used singly or in combination of two or more.

Examples of the isothiocyanate compound (C) include include aliphatic polyisothiocyanate compounds such as hexamethylene diisothiocyanate, lysine diisothiocyanate methyl ester, lysine triisothiocyanate, m-xylylene diisothiocyanate, bis(isothiocyanatomethyl)sulfide, bis(isothiocyanatoethyl)sulfide, and bis(isothiocyanatoethyl)disulfide; alicyclic polyisothiocyanate compounds such as isophoron diisothiocianate, bis(isothiocyanatomethyl)cyclohexane, dicyclohexylmethane diisothiocianate, cyclohexane diisothiocianate, methyl cyclohexane diisothiocianate, 2,5-bis(isothiocyanatomethyl)bicyclo-[2.2.1]-heptane, 2,6-bis(isothiocyanatomethyl)bicyclo-[2.2.1]-heptane, 3,8-bis(isothiocyanatomethyl)tricyclodecane, 3,9-bis(isothiocyanatomethyl)tricyclodecane, 4,8-bis(isothiocyanatomethyl)tricyclodecane, and 4,9-bis(isothiocyanatomethyl)tricyclodecane; aromatic polyisothiocyanate compounds such as tolylene diisocyanate, 4,4-diphenylmethane diisothiocyanate, and diphenyl disulfide-4,4-diisothiocyanate; and sulfur-containing heterocyclic polyisothiocyanate compounds such as 2,5-diisothiocyanatothiophene, 2,5-bis(isothiocyanatomethyl)thiophene, 2,5-isothiocyanatotetrahydrothiophene, 2,5-bis(isothiocyanatomethyl)tetrahydrothiophene, 3,4-bis(isothiocyanatomethyl)tetrahydrothiophene, 2,5-diisothiocyanato-1,4-dithiane, 2,5-bis(isothiocyanatomethyl)-1,4-dithiane, 4,5-diisothiocyanato-1,3-dithiolane, and 4,5-bis(isothiocyanatomethyl)-1,3-dithiolane. The isothiocyanate compound (C) may be used singly or in combination of two or more.

When the epoxy compound (A), the (meth)acrylate (B) and the iso(thio)cyanate compound (C) are reacted, a ratio ($\gamma/\alpha$) of number ($\gamma$) of moles of an iso(thio)cyanate group in the iso(thio)cyanate compound (C) with respect to number ($\alpha$) of moles of the (meth)acrylic acid (B) is preferably from 0.5 to 1.5, is more preferably from 0.8 to 1.2, and is still more preferably about 1.0.

When the above-described reactant and the iso(thio)cyanate compound (C) are reacted, a ratio ($\gamma/\delta$) of number ($\gamma$) of moles of an iso(thio)cyanate group in the iso(thio)cyanate compound (C) with respect to number ($\delta$) of moles of a hydroxy group in the above-described reactant is preferably from 0.5 to 1.5, is more preferably from 0.8 to 1.2, and is still more preferably about 1.0.

The (meth)acrylate (D) in the present disclosure is preferably a compound represented by the following general formula (1).

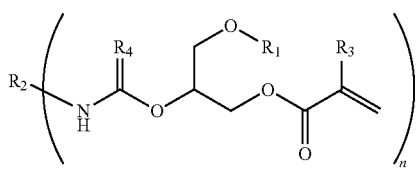
(1)

In general formula (1), $R_1$ represents a residue of the epoxy compound (A) from which the glycidyl ether group has been removed; $R_2$ represents a residue of the iso(thio)cyanate compound (C) from which all iso(thio)cyanate groups have been removed; $R_3$ represents a hydrogen atom or a methyl group; $R_4$ represents an oxygen atom or a sulfur atom; n is an integer of 2 or more; and plural instances of $R_1$, $R_3$ and $R_4$ may be the same or different, respectively.

In general formula (1), a residue of the epoxy compound (A) from which the glycidyl ether group has been removed in $R_1$, a structure containing a tertiary carbon atom or a quaternary carbon atom bonding to an oxygen atom in general formula (1) directly or via divalent linking group. A molecular weight of $R_1$ is preferably from 50 to 300.

$R_3$ is preferably a hydrogen atom.
$R_4$ is preferably an oxygen atom.
n is preferably 2 or 3, and is more preferably 2.

In general formula (1), $R_1$ is preferably a group represented by the following formula (2), (3), (4), (5), (6), (7), (8), (9) or (10), and is more preferably a group represented by formula (2). In formulae (2)-(10), each wavy line represents a binding site.

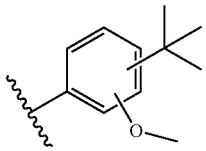
(2)

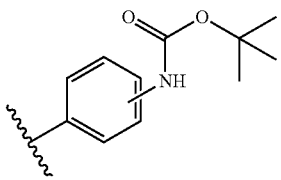
(3)

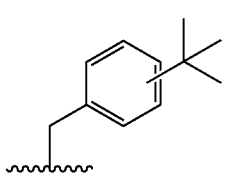
(4)

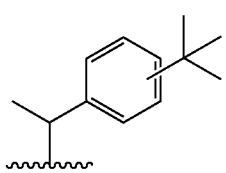
(5)

(6)

(7)

(8)

(9)

(10)

(Method of Manufacturing (Meth)Acrylate (D))

Hereinafter, a method of manufacturing the (meth)acrylate (D) in the present disclosure will be described. The method of manufacturing the (meth)acrylate (D) in the present disclosure includes a step of obtaining the reactant by reacting the epoxy compound (A) and the (meth)acrylic acid (B), and a step of obtaining the (meth)acrylate (D) that is a reaction product by reacting the above-described reactant and the iso(thio)cyanate compound (C).

The reaction of the epoxy compound (A) and the (meth)acrylic acid (B) may be carried out in the absence of solvent, or may be carried out in a solvent. As the solvent, a known solvent can be used as long as it is a solvent inert to the reaction, and examples thereof include hydrocarbon solvents such as n-hexane, benzene, toluene and xylene, ketone solvents such as acetone, methyl ethyl ketone and methyl isobutyl ketone, ester solvents such as ethyl acetate and butyl acetate, ether solvents such as diethyl ether, tetrahydrofuran and dioxane, halogen-based solvents such as dichloromethane, chloroform, carbon tetrachloride, 1,2-dichloroethane, and perclene, and polar solvents such as N,N-dimethylformamide, N,N-dimethylacetamide, N,N-dimethylimidazolidinone, dimethyl sulfoxide, sulfolane.

These solvents may be used singly or in combination of two or more.

When the epoxy compound (A) and the (meth)acrylic acid (B) are reacted, from the point of improving the reaction rate, a catalyst may be added. As a catalyst, a known catalyst to accelerate the reaction of an epoxy group of the epoxy compound (A) and a carboxy group of the (meth)acrylic acid (B) can be used. Examples of the catalyst include organophosphorus compounds such as triphenylphosphine, tertiary amines such as triethylamine and triethanolamine, quaternary ammonium salts such as trimethylammonium chloride and triethylbenzylammonium chloride, organophosphorus salts such as tetrabutylphosphonium bromide and tetraphenylphosphonium bromide, imidazoles such as 2-methylimidazole, and organometallic compounds such as cobalt octeneate.

An addition amount of a catalyst is preferably from 0.01% by mass to 10.0% by mass, and is more preferably from 0.01% by mass to 5.0% by mass, with respect to the total of the epoxy compound (A) and the (meth)acrylic acid (B).

A reaction temperature is not particularly limited, is usually from 0° C. to 200° C., and is preferably in a range of from 0° C. to 150° C.

Since a reaction time depends on the conditions such as the reaction temperature and the like, the reaction time is not particularly limited, and is usually from several minutes to several tens hours. Further, the reaction may be stopped at an arbitrary reaction rate while confirming the reaction rate by a known analytical means (for example, liquid chromatography, thin layer chromatography, infrared spectroscopy, and the like).

When the epoxy compound (A) and the (meth)acrylic acid (B) are reacted, from the point of suppressing the polymerization reaction between the (meth)acrylic acids (B), a polymerization inhibitor may be used. The polymerization inhibitor is not particularly limited, and examples thereof include dibutylhydroxytoluene (BHT), hydroquinone (HQ), hydroquinone monomethyl ether (MEHQ), and phenothiazine (PTZ).

A amount used of a polymerization inhibitor may be from 0.001% by mass to 0.5% by mass, may be from 0.002% by mass to 0.3% by mass, or may be from 0.005% by mass to 0.3% by mass, with respect to the total of the epoxy compound (A) and the (meth)acrylic acid (B).

The reaction of the above-described reactant the iso(thio)cyanate compound (C) may be carried out in the absence of solvent, or may be carried out in a solvent. As the solvent, a known solvent can be used as long as it is a solvent inert to the reaction, and for example, the above-described solvent can be used.

When the above-described reactant and the iso(thio)cyanate compound (C) are reacted, from the point of improving the reaction rate, a catalyst may be added. As a catalyst, a known catalyst to accelerate the reaction of a hydroxy group of the above-described reactant and an iso(thio)cyanate group of the iso(thio)cyanate compound (C) can be used. As a catalyst, it is preferable that a urethanization catalyst is added.

Examples of the urethanization catalyst include organic tin compounds such as dibutyltin dilaurate, dibutyltin dioctate, and tin octanoate, organometallic compounds other than tin such as copper naphthenate, cobalt naphthenate, zinc naphthenate, acetylacetonatozirconium, acetylacetonato iron, and acetylacetonatogermanium, amine compounds such as triethylamine, 1,4-diazabicyclo[2.2.2]octane, 2,6,7-trimethyl-1-diazabicyclo[2.2.2]octane, 1,8-diazabicyclo[5.4.0]undecene, N,N-dimethylcyclohexylamine, pyridine, N-methylmorpholin, N,N,N',N'-tetramethylethylenediamine, N,N,N',N'-tetramethyl-1,3-butanediamine, N,N,N',N'-pentamethyldiethylenetriamine, N,N,N', N'-tetra(3-dimethylaminopropyl)-methanediamine, N,N'-dimethylpiperazine, 1,2-dimethylimidazole and salts thereof, and trialkylphosphine compounds such as tri-n-butylphosphine, tri-n-hexylphosphine, tricyclohexylphosphine and tri-n-octylphosphine. Among these, dibutyltin dilaurate and tin octanate, which proceed favorably with a small amount and have high selectivity for the iso(thio)cyanate compound (C), are preferable.

An amount used of the urethanization catalyst may be from 0.001% by mass to 0.1% by mass, or may be from 0.01% by mass to 0.1% by mass, with respect to the total of the reactant and the iso(thio)cyanate compound (C).

A reaction temperature is not particularly limited, is usually from 20° C. to 120° C., and is preferably in a range of from 30° C. to 100° C.

Since a reaction time depends on the conditions such as the reaction temperature and the like, the reaction time is not particularly limited, and is usually from several minutes to several tens hours. Examples of the method for confirming the end point of the reaction include analysis by HPLC (high performance liquid chromatography).

Hereinafter, a modified example of the above-described (meth)acrylate (D) will be described. The (meth)acrylate (D) according to the modified example contains a (meth)acryloyloxy group, a urethane bond, and a structure represented by the following general formula (1-1). By using the (meth)acrylate (D) according to the modified example, it is possible to form the cured product with excellent breaking strength and make polymerization shrinkage less during curing.

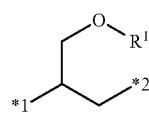

(1-1)

In general formula (1-1), $R^1$ is a structure containing a tertiary carbon atom or a quaternary carbon atom; and *1 and *2 represent a binding site.

The structure containing a tertiary carbon atom or a quaternary carbon atom may be the above-described structure containing a tertiary carbon atom or a quaternary carbon atom such as tert-butyl group, or may be the structure in which a divalent linking group such as a p-phenylene group is bonded to tert-butyl group or the like.

More specifically, the structure containing a tertiary carbon atom or a quaternary carbon atom may be a group represented by the above-described formula (2), (3), (4), (5), (6), (7), (8), (9) or (10).

The structure containing a tertiary carbon atom or a quaternary carbon atom may be a residue of the above-described epoxy compound (A) containing a glycidyl ether group, which is a functional group containing an epoxy group from which the glycidyl ether group has been removed.

The (meth)acrylate (D) according to the modified example may be a compound having the structure (hereinafter, it is also referred to as "structure (A)") represented by general formula (1-1), and further having the structure (hereinafter, it is also referred to as "structure (B)") in which *1 in general formula (1-1) is bonded to an oxygen atom of a urethane bond and *2 in general formula (1-1) is bonded to a (meth)acryloyloxy group.

The (meth)acrylate (D) according to the modified example preferably contains two or three structures (A), and more preferably contains two structures (A).

The (meth)acrylate (D) according to the modified example preferably contains two or three structures (A) and two or three structures (B), and more preferably contains two structures (A) and two structures (B).

[Monomer Composition]

A monomer composition in the present disclosure contains the (meth)acrylate (D) in the present disclosure. Further, the monomer composition in the present disclosure may contain a (meth)acrylate (hereinafter, it is also referred to as "(meth)acrylate (E)") other than the (meth)acrylate (D).

Examples of the (meth)acrylate (E) include neopentyl di(meth)acrylate, 1,4-butanediol di(meth)acrylate, 1,6-hexanediol di(meth)acrylate, 1,8-octanediol di(meth)acrylate, 1,9-nonanediol di(meth)acrylate, 1,10-decanediol di(meth)acrylate, tricyclodecanedimethanol di(meth)acrylate, ethylene glycol di(meth)acrylate, diethylene glycol di(meth)acrylate, triethylene glycol di(meth)acrylate, tetraethylene glycol di(meth)acrylate, polyethylene glycol di(meth)acrylate, tripropylene glycol di(meth)acrylate, tetrapropylene glycol di(meth)acrylate, polypropylene glycol di(meth)acrylate, 2,2-bis[4-(3-(meta)acryloyloxy-2-hydroxypropoxy)phenyl]propane, ethylene oxide-modified bisphenol A di(meth)acrylate, propylene oxide-modified bisphenol A di(meth)acrylate, and 2,2,4-trimethylhexamethylene bis(2-carbamoyloxyethyl)dimethacrylate (urethane dimethacrylate: UDMA). The (meth)acrylate (E) may be used singly or in combination of two or more. For example, in order to adjust a viscosity of the monomer composition to be low, a viscosity adjusting monomer such as triethylene glycol dimethacrylate may be used, and in order to attain high mechanical strength, urethane dimethacrylate may be further used in combination. When the viscosity adjusting monomer and urethane dimethacrylate are used in combination, the viscosity adjusting monomer and urethane dimethacrylate may be used in a mass ratio of 1:0.8 to 1.2.

A content of the (meth)acrylate (D) in the monomer composition is preferably from 5% by mass to 90% by mass, more preferably from 10% by mass to 80% by mass, and still more preferably from 30% by mass to 75% by mass.

A content of the (meth)acrylate (E) in the monomer composition is preferably from 10% by mass to 95% by mass, more preferably from 20% by mass to 90% by mass, and still more preferably from 25% by mass to 75% by mass.

[Molded Body]

A molded body in the present disclosure include a cured product of the monomer composition in the present disclosure. For example, by curing the monomer composition containing the (meth)acrylate (D), or preferably the monomer composition containing the (meth)acrylate (D) and the (meth)acrylate (E), it is possible to obtain the cured product with excellent breaking strength.

[Composition for Dental Material]

A composition for a dental material in the present disclosure contains the monomer composition in the present disclosure, a polymerization initiator, and a filler. This composition for a dental material has room temperature polymerizability, thermally polymerizability, or photo polymerizability, and can be preferably used as, for example, a dental restorative material.

A blending amount of monomer composition is preferably from 20% by mass to 80% by mass, and more preferably from 20% by mass to 50% by mass, with respect to 100% by mass of the composition for a dental material.

As the polymerization initiator, a general polymerization initiator used in the dental field can be used, and the polymerization initiator is usually selected in consideration of polymerizability and polymerization conditions of the polymerizable compounds such as the (meth)acrylate (A) and the (meth)acrylate (B) contained in the composition for a dental material.

When carrying out room temperature polymerization, as the polymerization initiator, for example, a redox-based polymerization initiator formed by a combination of an oxidizing agent and a reducing agent is preferable. When the redox-based polymerization initiator is used, the oxidizing agent and the reducing agent may be packaged separately, and both may be mixed just before use.

The oxidizing agent is not particularly limited, and examples thereof include organic peroxides such as diacyl peroxides, peroxyesters, dialkyl peroxides, peroxyketals, ketone peroxides and hydroperoxides. Examples of the organic peroxides include diacyl peroxides such as benzoyl peroxide, 2,4-dichlorobenzoyl peroxide, and m-toluoyl peroxide; peroxyesters such as t-butylperoxybenzoate, bis-t-butylperoxyisophthalate, 2,5-dimethyl-2,5-bis(benzoylperoxy)hexane, t-butylperoxy-2-ethylhexanoate, and t-butylperoxyisopropyl carbonate; dialkyl peroxides such as dicumyl peroxide, di-t-butyl peroxide, and lauroyl peroxide; peroxyketals such as 1,1-bis(t-butylperoxy)-3,3,5-trimethylcyclohexane; ketone peroxides such as methyl ethyl ketone peroxide; and hydroperoxides such as t-butyl hydroperoxide.

The reducing agent is not particularly limited, and usually a tertiary amine is used as the reducing agent. Examples of the tertiary amine include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-i-propylaniline, N,N-dimethyl-4-t-butylaniline, N,N-dimethyl-3,5-di-t-butylaniline, N,N-bis(2-hydroxyethyl)-p-toluidine, N,N-bis(2-hydroxyethyl)-3,5-dimethyl aniline, N,N-bis(2-hydroxyethyl)-3,4-dimethylaniline, N,N-bis(2-hydroxyethyl)-4-ethyl aniline, N,N-bis(2-hydroxyethyl)-4-i-propylaniline, N,N-bis(2-hydroxyethyl)-4-t-butylaniline, N,N-di(2-hydroxyethyl)-3,5-di-i-propylaniline, N,N-bis(2-hydroxyethyl)-3,5-di-t-butylaniline, ethyl 4-dimethylaminobenzoate, 2-butoxyethyl 4-dimethylaminobenzoate, (2-methacryloyloxy)ethyl 4-dimethylaminobenzoate, trimethylamine, triethylamine, N-methyldiethanolamine, N-ethyldiethanolamine, N-n-butyl diethanolamine, N-lauryldiethanolamine, triethanolamine, (2-dimethylamino)ethylmethacrylate, N,N-bis(methacryloyloxyethyl)-N-methylamine, N,N-bis(methacryloyloxyethyl)-N-ethylamine, N,N-bis(2-hydroxyethyl)-N-methacryloyloxyethylamine, N,N-bis(methacryloyl)oxyethyl)-N-(2-hydroxyethyl)amine, and tris(methacryloyloxyethyl) amine.

In addition to these organic peroxide/amine-based polymerization initiators, redox-based polymerization initiators such as cumenehydroperoxide/thiourea-based, ascorbic acid/$Cu^{2+}$ salt-based, and organic peroxide/amine/sulfinic acid (or salt thereof)-based can be used. as the polymerization initiator, tributylborane, organic sulfinic acid and the like are also preferably used.

When carrying out thermal polymerization by heating, the polymerization initiators such as peroxides and azo compounds are preferable.

The peroxide is not particularly limited, and example thereof include benzoyl peroxide, t-butyl hydroperoxide, and cumene hydroperoxide. The azo compound is not particularly limited, and example thereof include azobisisobutyronitrile.

When carrying out photopolymerization by visible light irradiation, redox-based initiators such as α-diketone/tertiary amine, α-diketone/aldehyde, and α-diketone/mercaptan are preferable.

Photopolymerization initiator is not particularly limited, and examples thereof include α-diketone/reducing agent, ketal/reducing agent, and thioxanthone/reducing agent. Examples of the α-diketone include camphorquinone, benzyl, and 2,3-pentandione. Examples of the ketal include benzyldimethyl ketal, and benzyldiethyl ketal. Examples of the thioxanthone include 2-chlorothioxanthone, and 2,4-diethylthioxanthone. Examples of the reducing agent include Michler's ketone; tertiary amines such as 2-(dimethylamino)ethyl methacrylate, N,N-bis[(meth)acryloyloxyethyl]-N-methylamine, ethyl-N,N-dimethylamino benzoate, butyl-4-dimethylamino benzoate, butoxyethyl-4-dimethylamino benzoate, N-methyl diethanolamine, 4-dimethylaminobenzophenone, N,N-bis(2-hydroxyethyl)-p-toluidine, and dimethylaminophenanthrol; aldehydes such as citronellal, laurylaldehyde, phthaldialdehyde, dimethylaminobenzaldehyde, and terephthalaldehyde; compounds containing a thiol group such as 2-mercaptobenzoxazole, decanethiol, 3-mercaptopropyltrimethoxysilane, 4-mercaptoacetophenone, thiosalicylic acid, and thiobenzoic acid. Polymerization initiators such as α-diketone/organic peroxide/reducing agent-based polymerization initiators prepared by adding the organic peroxide to these redox-based polymerization initiators are also preferably used.

When carrying out photopolymerization by ultraviolet irradiation, the photopolymerization initiators such as benzoin alkyl ether, and benzyl dimethyl ketal are preferable. The photopolymerization initiators of (bis)acylphosphine oxides are also preferably used.

Of the (bis)acylphosphine oxides, examples of acylphosphine oxides include 2,4,6-trimethylbenzoyl diphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, and benzoyldi-(2,6-dimethylphenyl)phosphonate. Examples of the (bis) acylphosphine oxides include bis-(2,6-dichlorobenzoyl) phenylphosphine oxide, bis-(2,6-dichlorobenzoyl)-2,5-dimethylphenylphosphine oxide, bis-(2,6-dichlorobenzoyl)-4-propyl phenylphosphine oxide, bis-(2,6-dichlorobenzoyl)-1-naphthylphosphine oxide, bis-(2,6-dimethoxybenzoyl) phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, and (2,5,6-trimethylbenzoyl)-2,4,4-trimethylpentylphosphine oxide. The photopolymerization initiators of these (bis) acylphosphine oxides may be used singly or in combination with reducing agents such as various amines, aldehydes, mercaptans and sulfinates. The photopolymerization initiators of these (bis)acylphosphine oxides may be used in combination with the above described visible light photopolymerization initiators.

The polymerization initiators described above may be used singly or in combination of two or more. A blending amount of the polymerization initiator is preferably from 0.01% by mass to 20% by mass, and more preferably from 0.1% by mass to 5% by mass, with respect to 100% by mass of the composition for a dental material.

As the filler, a general filler used in the dental field can be used. Fillers are usually roughly classified into organic fillers and inorganic fillers.

Examples of organic fillers include fine powders of polymethyl methacrylate, polyethylmethacrylate, methyl methacrylate-ethyl methacrylate copolymer, crosslinked polymethylmethacrylate, crosslinked polyethyl methacrylate, ethylene-vinyl acetate copolymer, and styrene-butadiene copolymer.

Examples of inorganic fillers include fine powders of various glasses (mainly silicon dioxide, and if necessary, containing oxides such as heavy metals, boron, and aluminum), various ceramics, diatomaceous earth, kaolin, clay minerals (montmorillonite, and the like), activated clay, synthetic zeolite, mica, calcium fluoride, ytterbium fluoride, calcium phosphate, barium sulfate, zirconium dioxide, titanium dioxide, and hydroxyapatite. Specific examples of these inorganic fillers include barium borosilicate glasses (Kimble Raysorb T3000, Shot 8235, Shot GM27884, Shot GM39923, and the like), strontium boroaluminosilicate glasses (Raysorb T4000, Shot G018-093, Shot GM32087, and the like), lantern glasses (Shot GM31684, and the like), fluoroaluminosilicate glasses (shot G018-091, shot G018-117, and the like), and boroaluminosilicate glasses containing zirconium, cesium, and the like (shot G018-307, G018-308, G018-310, and the like).

An organic-inorganic composite filler obtained by preliminarily adding a polymerizable compound to an inorganic filler to form a paste, then polymerizing and curing the polymerizable compound, and pulverizing the mixture may be used.

In the composition for a dental material, a composition mixed with a microfiller having a particle size of 0.1 μm or less is one of the preferred aspects for a dental composite resin. As the material of the filler having such a small particle size, silica (for example, trade name Aerosil), alumina, zirconia, titania and the like are preferable. The mixture of such an inorganic filler having a small particle size is advantageous in obtaining the polishing smoothness of the cured product of the composite resin.

These fillers may be surface-treated with a surface-treating agent such as a silane coupling agent, depending on the purpose. As the surface-treating agent, known silane coupling agents may be used, and for example organic silicon compounds such as methacryloxyalkyltrimethoxysilane (carbon number between methacryloxy group and silicon atom: 3 to 12), methacryloxyalkyltriethoxysilane (carbon number between methacryloxy group and silicon atom: 3 to 12), vinyl trimethoxysilane, vinyl ethoxysilane, and vinyl triacetoxysilane may be used. An amount of the surface-treating agent is preferably from 0.1% by mass to 20% by mass, and more preferably from 1% by mass to 10% by mass, with respect to 100% by mass of the filler before surface treatment.

These fillers may be used singly or in combination of two or more. A blending amount of the filler may be appropriately determined in consideration of the operability (viscosity) of the composition for a dental material (for example, composite resin paste), the mechanical property of the cured product, and the like. The blending amount of the filler is preferably from 10 parts by mass to 2000 parts by mass, more preferably from 50 parts by mass to 1000 parts by mass, and further preferably from 100 parts by mass to 600 parts by mass, with respect to 100 parts by mass of the all components other than the filler contained in the composition for a dental material.

The composition for a dental material in the present disclosure may appropriately contain the monomer composition in the present disclosure, a polymerization initiator, and the component other than a filler, depending on the purpose. For example, the above described polymerization inhibitor for improving storage stability may be contained. In order to adjust a color tone, a pigment such as a known pigment or dye may be contained. In order to improve the strength of the cured product, a reinforcing material such as known fiber may be contained. The composition for a dental material in the present disclosure may contain additives such as a bactericide, a disinfectant, a stabilizer, and a preservative as long as the effect of the present invention is exhibited.

The composition for a dental material in the present disclosure can be cured under appropriate conditions in the polymerization method of the above described polymerization initiator. For example, in the case of the composition for a dental material in the present disclosure containing a photopolymerization initiator by visible light irradiation, a desired cured product can be obtained by processing the composition for a dental material into a predetermined shape, and then irradiating the processed composition with visible light for a predetermined time using a known light irradiation device. Conditions such as irradiation intensity and irradiation intensity can be appropriately changed according to the curability of the composition for a dental material. Further, the mechanical property of the cured product may be improved by heat-treating the cured product cured by light irradiation such as visible light irradiation, under more appropriate conditions.

The cured product, obtained as described above, of the composition for a dental material in the present disclosure is preferably used as the dental material.

The method of using the composition for a dental material in the present disclosure is not particularly limited as long as it is generally known as a method of using a dental material. For example, when the composition for a dental material in the present disclosure is used as a composite resin for filling a caries cavity, the purpose can be achieved by filling the cavity in the oral cavity with the composition for a dental material and then photocured using a known light irradiation device. When the composition is used as a composite resin for a crown, the desired crown material can be obtained by processing the composition for a dental material into a predetermined shape, and then photocured using a known light irradiation device, and further carrying out heat treatment under predetermined conditions.

The composition for a dental material and the dental material in the present disclosure can be preferably used as, for example, a dental restorative material, a denture base resin, a denture base lining material, an impression material, a joint wearing material (resin cement, resin-added glass ionomer cement and the like), a dental adhesive (an orthodontic adhesive, a cavity coating adhesive and the like), a tooth fissure sealant, resin block for CAD/CAM, temporary crown, and an artificial tooth material. When the dental restorative material is classified according to the applicable range, it can be classified into a composite resin for a crown, a composite resin for filling a caries cavity, a composite resin for abutment construction, a composite resin for filling restoration, and the like. Among these, the composition for a dental material and the dental material in the present disclosure are particularly suitable for dental restorative materials such as composite resins.

[Dental Material]

A dental material in the present disclosure includes a cured product of the composition for a dental material in the present disclosure. The curing conditions of the composition for a dental material may be appropriately determined according to the composition of the composition for a dental material, the use of the dental material, and the like.

EXAMPLES

The invention will now be described more concretely by way of examples thereof; however, the invention is not limited to the following examples.

The abbreviations of the compounds used in the examples of the present invention are shown below.

UDMA: 2,2,4-trimethylhexamethylenebis (2-carbamoyloxyethyl) dimethacrylate
3G: triethylene glycol dimethacrylate
TBG: tert-butyl glycidyl ether
BPG: 4-tert-butylphenyl glycidyl ether
OPG: 4-tert-octylphenyl glycidyl ether
CPG: 4-cumylphenyl glycidyl ether
IPDI: isophorone diisocyanate
XDI: m-xylylene diisocyanate
TBAB: tetrabutyl ammonium bromide
DBTDL: dibutyl tin dilaurate
BHT: dibutylhydroxytoluene
CQ: camphorquinone
DMAB2-BE: 2-butoxyethyl 4-dimethylaminobenzoate

[Method of Measuring IR Spectrum]

IR spectrum of (meth)acrylate obtained in each example was measured by using Fourier Transform Infrared Spectroscopy, Spectrum Two/UATR (Universal Attenuated Total Reflectance) manufactured by PerkinElmer Japan Co., Ltd.

The (meth)acrylate obtained in each example was left to stand at 20° C., for 24 hours, and then the infrared absorption spectrum of the (meth)acrylate was measured at 20° C.

[Method of Bending Test]

The method of a bending test in the examples and the comparative examples in the present invention is shown below.

(Preparation of Test Piece for Bending Test)

The composition for a dental material was prepared by adding 0.05 parts by mass of CQ and 0.05 parts by mass of DMAB2-BE to 10 parts by mass of the monomer composition obtained in each example and comparative example, stirring the mixture at room temperature until uniform, further adding 15 parts by mass of silica glass (Fusedex-X (Tatsumori Co., Ltd.)), stirring the mixture using a mortar until uniform, and then defoaming the mixture. The obtained composition for a dental material was placed in a stainless steel mold of 2 mm×2 mm×25 mm, and light was irradiated for 3 minutes on each side, that is, for 6 minutes on both sides using a visible light irradiation device (Solidayite V manufactured by Shofu Inc.). Further, the test piece taken out from the stainless steel mold was heat-treated in an oven at 130° C. for 2 hours. After cooling the test piece taken out from the oven to room temperature, the test piece was immersed in distilled water in a sealable sample bottle and held at 37° C. for 24 hours. The test piece after immersed was used as the test piece (test piece for bending test).

(Bending Test)

A three-point bending test was carried out by using the test piece prepared by the above method and a testing machine (Autograph EZ-S manufactured by Shimadzu Corporation) at a distance between fulcrums of 20 mm and a crosshead speed of 1 mm/min.

[Method for Measuring Polymerization Shrinkage Rate]

The method for measuring polymerization shrinkage rate in Examples and Comparative Examples according to the present invention is shown below.

(Preparation of Sample for Measuring Polymerization Shrinkage Rate)

The composition for measuring polymerization shrinkage rate was prepared by adding 0.1 parts by mass of CQ and 0.1 parts by mass of DMAB2-BE to 20 parts by mass of the monomer composition obtained in each example and comparative example, stirring the mixture at room temperature until uniform. The obtained composition for measuring polymerization shrinkage rate was filled in a silicon mold with a diameter of 10 mm and a depth of 2 mm and after sandwiching it from above and below with the cover glass, light was irradiated for 3 minutes on each side, that is, for 6 minutes on both sides using a visible light irradiation device (Solidayite V manufactured by Shofu Inc.). The test piece was taken out from the mold, and the test piece whose surface was wiped with acetone was used as a test sample (sample for measuring polymerization shrinkage rate).

(Measurement of Polymerization Shrinkage Rate)

The density of the monomer composition before and after curing was measured using a dry densitometer (Accupic 1330 manufactured by Shimadzu Corporation), and polymerization shrinkage rate was determined from the following formula (1).

polymerization shrinkage rate (%)=((density after polymerization−density before polymerization)/density after polymerization)×100  Formula (1):

Next, polymerization shrinkage rate of 3G alone was measured by the same operation as above. As a result, the polymerization shrinkage rate was 14.3%.

Next, using polymerization shrinkage rate (S1) of the monomer composition obtained in each Example and Comparative Example and the polymerization shrinkage rate (S2, 14.3%) of 3G alone, polymerization shrinkage rate (S3) of urethane acrylates (A-1) to (A-13) and UDMA was determined from the following formula (2).

(S3)=((S1)−((S2)×0.3))/0.7  Formula (2):

Production Example 1

3.8 parts by mass of TBAB, 101 parts by mass of acrylic acid, and 182.2 parts by mass of TBG were charged in a 100 mL 4-neck flask equipped with a well-dried stirring blade and a thermometer, and after dissolving them to make a homogeneous solution, the temperature of the solution was raised to 100° C. The reaction was carried out for 12 hours while maintaining the reaction temperature at from 100° C. to 110° C. After completion of the reaction, the reaction solution was cooled to room temperature, and 400 mL of toluene was added. The obtained toluene solution was transferred to a 1000 mL separatory funnel and washed with distilled water until the pH of the aqueous phase became neutral. After washing with water, 0.56 parts by mass of BHT was charged and mixed and dissolved. Then, toluene was distilled off from the toluene phase using an evaporator to obtain 216 g of modified hydroxyacrylate-1 (HA-1).

Production Example 2

3.0 parts by mass of TBAB, 77.35 parts by mass of acrylic acid, and 202 parts by mass of BPG were charged in a 100 mL 4-neck flask equipped with a well-dried stirring blade and a thermometer, and after dissolving them to make a homogeneous solution, the temperature of the solution was raised to 100° C. The reaction was carried out for 18 hours while maintaining the reaction temperature at from 100° C. to 110° C. After completion of the reaction, the reaction solution was cooled to room temperature, and 400 mL of toluene was added. The obtained toluene solution was transferred to a 1000 mL separatory funnel and washed with distilled water until the pH of the aqueous phase became neutral. After washing with water, 0.56 parts by mass of BHT was charged and mixed and dissolved. Then, toluene was distilled off from the toluene phase using an evaporator to obtain 264 g of modified hydroxyacrylate-2 (HA-2).

Production Example 3

3.0 parts by mass of TBAB, 77.35 parts by mass of acrylic acid, and 257 parts by mass of OPG were charged in a 100 mL 4-neck flask equipped with a well-dried stirring blade and a thermometer, and after dissolving them to make a homogeneous solution, the temperature of the solution was raised to 100° C. The reaction was carried out for 22 hours while maintaining the reaction temperature at from 100° C. to 110° C. After completion of the reaction, the reaction solution was cooled to room temperature, and 400 mL of toluene was added. The obtained toluene solution was transferred to a 1000 mL separatory funnel and washed with distilled water until the pH of the aqueous phase became neutral. After washing with water, 0.56 parts by mass of BHT was charged and mixed and dissolved. Then, toluene was distilled off from the toluene phase using an evaporator to obtain 308 g of modified hydroxyacrylate-3 (HA-3).

Production Example 4

3.0 parts by mass of TBAB, 77.35 parts by mass of acrylic acid, and 263 parts by mass of CPG were charged in a 100 mL 4-neck flask equipped with a well-dried stirring blade and a thermometer, and after dissolving them to make a homogeneous solution, the temperature of the solution was raised to 100° C. The reaction was carried out for 22 hours while maintaining the reaction temperature at from 100° C. to 110° C. After completion of the reaction, the reaction solution was cooled to room temperature, and 400 mL of toluene was added. The obtained toluene solution was transferred to a 1000 mL separatory funnel and washed with distilled water until the pH of the aqueous phase became neutral. After washing with water, 0.56 parts by mass of BHT was charged and mixed and dissolved. Then, toluene was distilled off from the toluene phase using an evaporator to obtain 306 g of modified hydroxyacrylate-4 (HA-4).

Production Example 5

3.0 parts by mass of TBAB, 84.30 parts by mass of methacrylic acid, and 202 parts by mass of BPG were charged in a 100 mL 4-neck flask equipped with a well-dried stirring blade and a thermometer, and after dissolving them to make a homogeneous solution, the temperature of the solution was raised to 100° C. The reaction was carried out for 18 hours while maintaining the reaction temperature at from 100° C. to 110° C. After completion of the reaction, the reaction solution was cooled to room temperature, and 400 mL of toluene was added. The obtained toluene solution was transferred to a 1000 mL separatory funnel and washed with distilled water until the pH of the aqueous phase became neutral. After washing with water, 0.56 parts by mass of BHT was charged and mixed and dissolved. Then, toluene was distilled off from the toluene phase using an evaporator to obtain 258 g of modified hydroxymethacrylate-1 (HM-1).

Example 1

0.03 parts by mass of DBTDL, and 13.73 parts by mass of IPDI were charged in a 100 mL 4-neck flask equipped with a well-dried stirring blade and a thermometer, and after dissolving them to make a homogeneous solution, the temperature of the solution was raised to 80° C., and further 25.0 parts by mass of HA-1 was added dropwise over 1 hour. Since the internal temperature increased due to the heat of reaction during the dropping, the dropping amount was controlled so as to be 90° C. or lower. After dropping the entire amount of HA-1, the reaction was carried out for 5 hours while maintaining the reaction temperature at 90° C. At this time, the progress of the reaction was followed by HPLC analysis to confirm the end point of the reaction. By discharging the product from the reactor, 38 g of urethane diacrylate (A-1) as the (meth)acrylate (D) was obtained. IR spectrum of urethane diacrylate (A-1) is shown in FIG. 1. 10.5 parts by mass of the obtained urethane diacrylate (A-1) and 4.5 parts by mass of 3G were placed in a container and stirred at 50° C. until uniform to obtain monomer composition (1). By using the obtained monomer composition (1), the composition (1) for a dental material, and the test piece (test piece for bending test) were obtained according to the methods described in the sections of (Preparation of Test Piece for Bending Test) and (Bending Test). When the bending test was carried out, the elastic modulus was 6410 MPa, and the breaking strength was 155 MPa. By using the obtained monomer composition (1), the composition (1) for measuring polymerization shrinkage rate and the test sample (sample for measuring polymerization shrinkage rate) were obtained according to the methods described in the sections of (Preparation of Sample for Measuring Polymerization Shrinkage Rate) and (Measurement of Polymerization Shrinkage Rate). When the measurement of polymerization shrinkage rate was carried out, the polymerization shrinkage rate was 2.60%.

Examples 2 to 14

Urethane diacrylates (A-2) to (A-12), and urethane dimethacrylates (M-1) to (M-2) were obtained in the same manner as Example 1 except that the modified hydroxy acrylate compound and the isocyanate compound were changed to the compounds and amounts shown in Table 1. IR spectrums of urethane diacrylates (A-2) to (A-12), and urethane dimethacrylates (M-1) to (M-2) are shown in FIG. 2 to FIG. 14. Monomer compositions (2) to (14) were obtained in the same manner as Example 1 except that urethane diacrylate (A-1) was respectively changed to urethane diacrylates (A-2) to (A-12), and urethane dimethacrylates (M-1) to (M-2). By using the obtained monomer compositions (2) to (14), the compositions (2) to (14) for a dental material, and the test pieces (tests piece for bending test) were obtained according to the methods described in the sections of (Preparation of Test Piece for Bending Test) and (Bending Test), and then the bending test was carried out. The elastic modulus, the breaking strength, and the breaking energy are shown in Table 1. Further, by using the obtained monomer compositions (2) to (14), the compositions (2) to (14) for measuring polymerization shrinkage rate and the test samples (samples for measuring polymerization shrinkage rate) were obtained according to the methods described in the sections of (Preparation of Sample for Measuring Polymerization Shrinkage Rate) and (Measurement of Polymerization Shrinkage Rate), and then the measurement of polymerization shrinkage rate was carried out. The polymerization shrinkage rate is shown in Table 1.

Comparative Example 1

0.03 parts by mass of DBTDL, and 11.63 parts by mass of XDI were charged in a 100 mL 4-neck flask equipped with a well-dried stirring blade and a thermometer, and after dissolving them to make a homogeneous solution, the temperature of the solution was raised to 80° C., and further 27.8 parts by mass of 3-phenoxy-2-hydroxyacrylate (HA-5) was added dropwise over 1 hour. Since the internal temperature increased due to the heat of reaction during the dropping, the dropping amount was controlled so as to be 90° C. or lower. After dropping the entire amount of HA-5, the reaction was carried out for 5 hours while maintaining the reaction temperature at 90° C. At this time, the progress of the reaction was followed by HPLC analysis to confirm the end point of the reaction. By discharging the product from the reactor, 39 g of urethane diacrylate (A-15) was obtained. 10.5 parts by mass of the obtained urethane diacrylate (A-15) and 4.5 parts by mass of 3G were placed in a container and stirred at 50° C. until uniform to obtain monomer composition (15). By using the obtained monomer composition (15), the composition (15) for a dental material, and the test piece (test piece for bending test) were obtained according to the methods described in the sections of (Preparation of Test Piece for Bending Test) and (Bending Test). When the bending test was carried out, the elastic modulus was 6880 MPa, and the breaking strength was 132 MPa. By using the obtained monomer composition (15), the composition (15) for measuring polymerization shrinkage rate and the test sample (sample for measuring polymerization shrinkage rate) were obtained according to the methods described in the sections of (Preparation of Sample for Measuring Polymerization Shrinkage Rate) and (Measurement of Polymerization Shrinkage Rate). When the measurement of polymerization shrinkage rate was carried out, the polymerization shrinkage rate was 2.94%.

Comparative Example 2

Monomer composition (16) was obtained in the same manner as Example 1 except that urethane diacrylate (A-1) was changed to UDMA. By using the obtained monomer composition (16), the composition (16) for a dental material, and the test piece (test piece for bending test) were obtained according to the methods described in the sections of (Preparation of Test Piece for Bending Test) and (Bending Test). When the bending test was carried out, the elastic modulus was 5890 MPa, and the breaking strength was 123 MPa. By using the obtained monomer composition (16), the composition (16) for measuring polymerization shrinkage rate and the test sample (sample for measuring polymerization shrinkage rate) were obtained according to the methods described in the sections of (Preparation of Sample for Measuring Polymerization Shrinkage Rate) and (Measurement of Polymerization Shrinkage Rate). When the measurement of polymerization shrinkage rate was carried out, the polymerization shrinkage rate was 7.50%.

TABLE 1

| | | Preparation ratio | | Property of (meth)acrylate | Cured product properties | |
|---|---|---|---|---|---|---|
| | | Hydroxy(meth)acrylate (parts by mass) | Isocyanate (parts by mass) | Polymerization Shrinkage Rate [%] | Elastic modulus [MPa] | Breaking strength [MPa] |
| Examples | 1 | HA-1 25.0 | I-1 13.73 | 2.60 | 6410 | 155 |
| | 2 | HA-1 25.0 | I-2 11.63 | 3.90 | 6810 | 190 |
| | 3 | HA-1 25.0 | I-3 12.99 | 4.60 | 6790 | 162 |
| | 4 | HA-1 25.0 | I-4 12.74 | 3.01 | 6790 | 180 |
| | 5 | HA-2 25.3 | I-2 8.65 | 2.59 | 7880 | 167 |
| | 6 | HA-2 27.5 | I-3 10.5 | 3.01 | 7070 | 153 |
| | 7 | HA-2 27.5 | I-4 10.3 | 1.87 | 7330 | 147 |
| | 8 | HA-2 27.5 | I-5 12.2 | 1.87 | 7460 | 132 |
| | 9 | HA-2 27.84 | I-6 9.7 | 2.01 | 7820 | 150 |
| | 10 | HA-2 25.7 | I-7 7.1 | 3.01 | 6840 | 132 |
| | 11 | HA-3 28.09 | I-2 7.86 | 2.36 | 8020 | 172 |
| | 12 | HA-2 28.60 | I-2 7.86 | 2.12 | 8370 | 162 |
| | 13 | HM-1 28.94 | I-2 9.31 | 3.44 | 6930 | 152 |
| | 14 | HM-1 28.94 | I-4 10.2 | 1.87 | 7420 | 143 |
| Comparative Examples | 1 | HA-5 27.8 | I-2 11.63 | 2.94 | 6880 | 132 |
| | 2 | — | — | 7.50 | 5890 | 123 |

HA-1 to HA-5, HM-1, I-1 to I-7 in Table 1 are as follows.
HA-1: modified hydroxyacrylate-1 synthesized by the method described in Production Example 1
HA-2: modified hydroxyacrylate-2 synthesized by the method described in Production Example 2
HA-3: modified hydroxyacrylate-3 synthesized by the method described in Production Example 3
HA-4: modified hydroxyacrylate-4 synthesized by the method described in Production Example 4
HA-5: 3-phenoxy-2-hydroxyacrylate
HM-1: modified hydroxy methacylate synthesized by the method described in Production Example 5
I-1: isophorone diisocyanate
I-2: m-xylylene diisocyanate
I-3: mixture of 2,2,4-trimethylhexamethylene diisocyanate and 2,4,4-trimethylhexamethylene diisocyanate
I-4: mixture of 2,5-bis(isocyanatemethyl)bicyclo[2.2.1]heptane and 2,6-bis(isocyanatemethyl)bicyclo[2.2.1]heptane
I-5: 1,3-Tetramethylxylylene diisocyanate
I-6: 1,3-bis(isocyanatemethyl)cyclohexane
I-7: 1,5-pentamethylene diisocyanate As shown in Table 1, the monomer compositions of Examples 1 to 14 were able to reduce the polymerization shrinkage rate as compared with the monomer compositions of Comparative Example 2, and were excellent in breaking strength. Further, the cured products in the monomer compositions of Examples 2, 5, 11, 12 and 13 using the same isocyanate (I-2) as the monomer composition of Comparative Example 1, were excellent in breaking strength as compared with the cured product in the monomer composition of Comparative Example 1.

The disclosures of Japanese Patent Application No. 2018-231945 filed on Dec. 11, 2018, are hereby incorporated by reference in its entirety.

All the documents, patent applications and technical standards that are described in the present specification are hereby incorporated by reference to the same extent as if each individual document, patent application or technical standard is concretely and individually described to be incorporated by reference.

The invention claimed is:

1. A (meth)acrylate comprising a compound (X) having a structure formed by a reaction of an epoxy compound (A) containing an epoxy group and a tertiary carbon atom or a quaternary carbon atom, a (meth) acrylic acid (B), and an iso(thio)cyanate compound (C) having two or more iso(thio)cyanate groups,
wherein the epoxy compound (A) comprises a tert-butyl group, a tert-pentyl group, a tert-hexyl group, a tert-heptyl group, a tert-octyl group, a tert-nonyl group, a tert-decyl group or a cumyl group, or wherein the (meth)acrylate is represented by the following general formula (1);

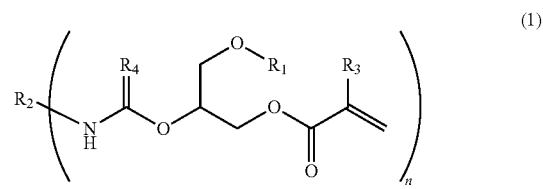

(1)

wherein, in general formula (1), $R_1$ represents a residue of the epoxy compound (A) from which the glycidyl ether group has been removed; $R_2$ represents a residue of the iso(thio)cyanate compound (C) from which all iso(thio)cyanate groups have been removed; $R_3$ represents a hydrogen atom or a methyl group; $R_4$ represents an oxygen atom or a sulfur atom; n is an integer of 2 or more; and plural instances of $R_1$, $R_3$ and $R_4$ may be the same or different, respectively.

2. The (meth)acrylate according to claim 1, wherein the compound (X) is a reaction product of a reactant of the epoxy compound (A) and the (meth) acrylic acid (B), and the iso(thio)cyanate compound (C).

3. The (meth)acrylate according to claim 1, wherein a molecular weight of the $R_1$ is from 50 to 300 in general formula (1).

4. The (meth)acrylate according to claim 1, wherein $R_1$ is a group represented by the following formula (2), (3), (4), (5), (6), (7), (8), (9) or (10) in general formula (1):

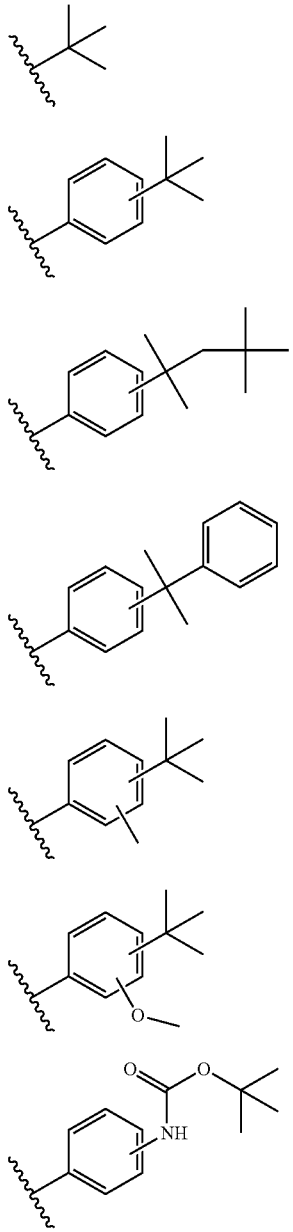

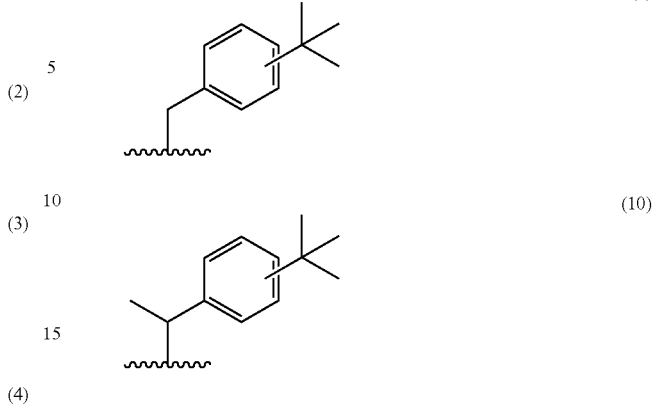

wherein, in formulae (2)-(10), each wavy line represents a binding site.

5. The (meth) acrylate according to claim 1, wherein the iso(thio)cyanate compound (C) is at least one kind of iso(thio)cyanate compound selected by the group consisting of hexamethylene diisocyanate, 2,2,4-trimethylhexamethylene diisocyanate, 2,4,4-trimethylhexamethylene diisocyanate, pentamethylene diisocyanate, m-xylylene diisocyanate, 1,3-tetramethylxylylene diisocyanate, isophorone diisocyanate, bis(isocyanatomethyl)cyclohexane, bis(isocyanatocyclohexyl)methane, 2,5-bis(isocyanatomethyl)bicyclo-[2.2.1]-heptane, 2,6-bis(isocyanatomethyl)bicyclo-[2.2.1]-heptane, tolylene diisocyanate, phenylene diisocyanate, and 4,4'-diphenylmethane diisocyanate.

6. A monomer composition comprising a (meth)acrylate (D) that is the (meth)acrylate according to claim 1.

7. A molded body comprising a cured product of the (meth)acrylate according claim 1.

8. A composition for a dental material comprising the (meth)acrylate according to claim 1, a polymerization initiator, and a filler.

9. A dental material comprising a cured product of the composition for a dental material according to claim 8.

10. A molded body comprising a cured product of the monomer composition according to claim 6.

11. A composition for a dental material comprising the monomer composition according to claim 6, a polymerization initiator, and a filler.

12. A dental material comprising a cured product of the composition for a dental material according to claim 11.

* * * * *